United States Patent [19]

Nagabhushan et al.

[11] 4,337,335

[45] Jun. 29, 1982

[54] TRANSITION METAL SALT COMPLEXES OF POLYAMINO ORGANIC COMPOUNDS

[75] Inventors: Tattanahalli L. Nagabhushan, Parsippany; William N. Turner, Bloomfield; Alan Cooper, West Caldwell, all of N.J.

[73] Assignee: Schering Corporation, Kenilworth, N.J.

[21] Appl. No.: 106,987

[22] Filed: Dec. 26, 1979

Related U.S. Application Data

[60] Division of Ser. No. 906,895, May 18, 1978, Pat. No. 4,230,847, which is a continuation-in-part of Ser. No. 697,297, Jun. 17, 1976, Pat. No. 4,136,254.

[51] Int. Cl.$^3$ .................... C07F 1/08; C07H 15/22; C07H 11/00; C07H 23/00
[52] U.S. Cl. ................. 536/13.6; 260/429 J; 260/429 R; 260/439 R; 260/438.1; 536/121; 536/13.7; 536/13.9; 536/16.8
[58] Field of Search ............. 536/10, 17 R, 121, 18; 260/429 J, 429 R, 338.1, 439 R

[56] References Cited

U.S. PATENT DOCUMENTS 3,388,141  6/1968  Berenbaum .................. 260/429 J
3,787,464  1/1974  Neri et al. .................... 260/429 J
4,044,036  8/1977  Hari et al. .................... 260/438.1
4,072,700  2/1978  Bohler et al. ................. 260/438.1
4,113,759  9/1978  Papenfuhs et al. ........... 260/438.1
4,138,480  2/1979  Gosalvez ........................ 536/121
4,206,139  6/1980  Idelson et al. ................ 260/438.1

OTHER PUBLICATIONS

Nasanen et al., "Suom Kemistilehti B.", vol. 42, No. 9, pp. 357–360, 1969.
Nasanen et al., "Suom Kemistilehti B.", vol. 43, No. 4, pp. 154–157, 1970.
Zimmerman, "The Preparation and Properties of Copper (II) and Nickel (II) Complexes of Alkanol Substituted Ethylene Diamines", West Virginia University 1969, University Microfilms, Inc., Ann Arbor, Michigan, pp. 1–130.

*Primary Examiner*—Johnnie R. Brown
*Attorney, Agent, or Firm*—Gerald S. Rosen; Bruce M. Eisen; Mary S. King

[57] ABSTRACT

Described are transition metal salt complexes of available neighboring amino and hydroxyl group pairs in polyamino organic compounds, their preparation, and use as intermediates in the preparation of selectively N-blocked polyamino organic compounds.

12 Claims, No Drawings

TRANSITION METAL SALT COMPLEXES OF POLYAMINO ORGANIC COMPOUNDS

CROSS-REFERENCE TO RELATED APPLICATION

This application is a division of our co-pending application Ser. No. 906,895 filed May 18, 1978, now U.S. Pat. No. 4,230,847, in turn a continuation-in-part of application Ser. No. 697,297 filed June 17, 1976, now U.S. Pat. No. 4,136,254.

FIELD OF INVENTION

This invention relates to a novel process useful particularly in carrying out aminocyclitol-aminoglycoside transformations, and to novel derivatives produced thereby and their use as intermediates.

More particularly, this invention relates to a process of selectively blocking certain amino groups in a polyamino organic compound utilizing as intermediates, novel transition metal salt complexes of available neighboring hydroxyl and amino group pairs in said polyamino organic compound. This invention also relates to novel, selectively blocked-amine derivatives produced thereby which are useful as intermediates whereby process improvements are effected.

Specifically, this invention relates to a process for preparing selectively blocked amino derivatives of aminocyclitolaminoglycosides, useful as intermediates in preparing other aminocyclitol-aminoglycoside derivatives having antibacterial activity, which comprises preparing, in situ, transition metal salt complexes of available neighboring amino and hydroxyl functions in said aminocyclitol-aminoglycoside, followed by introduction of acyl blocking groups on the non-complexed amino functions, thence removal of the transition metal salt cations. This invention also includes novel divalent transition metal salt complexes of said aminocyclitol-aminoglycosides as well as novel selectively blocked-amine derivatives of said aminocyclitol-aminoglycosides and their use as intermediates.

PRIOR ART

When carrying out certain chemical transformations of a polyamino-organic compound, particularly those in the carbohydrate and aminocyclitol-aminoglycoside art, in order to obtain good yields of a desired product, it is necessary to first prepare derivatives of amino functions in the molecule with "blocking" or "protecting" groups to prevent the amino functions from entering into competing reactions with the reagents being employed. Commonly employed blocking groups are acyl blocking groups which are easily attached to amino groups and can be removed after the desired transformation has been completed but which are stable under the reaction conditions to be employed.

Chemical transformations at a site other than at an amino function in a polyamino-organic compound usually involves the preparation of a per-N-acylated intermediate by reaction of the polyamino-organic compound with excess acylating reagent, followed by chemical transformation of the per-N-acylated intermediate and thence removal of the N-acyl protecting groups by methods well known in the art.

Chemical transformations in a polyamino-organic compound wherein the site of reaction is to be one of the amino functions, are ideally carried out on intermediates wherein every other amino function is selectively protected by a blocking group; otherwise, mixtures of various mono-N- and poly-N- derivatives are formed which require tedious separation techniques (usually chromatography or several chromatographies) to isolate the desired transformation product. However, it is not always possible to prepare the ideal selectively blocked intermediate by prior art methods so that, with amino functions unprotected, the desired transformation product is produced only in low yields.

When a polyamino-organic compound contains amino functions of various degrees of reactivity due either to steric factors and/or to the primary and/or secondary and/or tertiary nature of the amine groups, it is sometimes possible, although in moderate to low yields, to selectively protect some amino functions while leaving other amino functions unprotected at which a desired reaction may take place. Such procedures usually involve multistep transformations requiring the isolation and purification of each intermediate. Frequently, it is impossible to protect all amino functions other than the one at which a transformation is desired, such as, for example, when two amino functions are of equal reactivity, so that at best only some amino functions are blocked which minimizes the number of products formed in a given reaction but which still will give rise to a mixture of products resulting in poor yields of desired products isolatable and purifiable only with difficulty.

By our invention, it is now possible to easily prepare, in good yields, selectively blocked amino derivatives of polyamino organic compounds in which at least one amino function has an available neighboring hydroxyl group, by a one vessel-two-step procedure comprising the reaction in an inert organic solvent of said polyamino organic compound with a divalent transition metal salt followed by the reaction in situ of the novel polyamino-organic compound-transition metal salt complex thereby formed with an acylating agent whereby N-acyl derivatives of the non-complexed amino functions are formed. Upon removal of the transition metal cation from the complex, there are produced selectively blocked N-acyl derivatives of said polyamino organic compound which are easily isolated in good yields of high purity product or which can be further reacted in situ prior to isolation and removal of the acyl blocking groups. By slight modifications in the choice of solvent and/or in the relative molar quantities of transition metal salt or acylating agent employed, one can regulate which and how many amino functions are N-acylated.

Our invention finds its greatest use in the carbohydrate and aminocyclitol-aminoglycoside art whereby it is now possible to easily prepare in good yields N-acylated derivatives heretofore impossible to make or heretofore produced only in small quantities. Additionally, by our process, it is possible to remove the transition metal cation from the reaction mixture by precipitation as the sulfide salt and separation by filtration so that the resulting filtrate comprising the selectively N-acylated polyamino-organic compound is of sufficient purity and predictable yield to allow further reactions to be carried out without isolation of the N-acylated polyamino intermediate.

Prior to our invention, divalent transition metal salt complexes of neighboring amino and hydroxyl group pairs were unknown. The prior art postulates (Bull. Chem. Soc. Japan, Vol. 39, No. 6, 1235–1248 (1966)) the existence of cupraammonium complexes between amines on a chiral center and adjacent vicinal hydroxyl groups on a chiral center in situ in dilute aqueous ammonia solutions, said cupraammonium complexes being used for optical rotatory studies as an analytical tool in determining the absolute spatial relationship between vicinal amino/hydroxyl group pairs. The prior art cupraammonium complexes of vicinal amino/hydroxyl group pairs are described as being formed only in water in the presence of excesses of cupraammonium ion and are used only to measure optical rotation or circular dichroism.

By our invention, we have discovered that divalent transition metal salt complexes (including copper (II) complexes) of neighboring amino/hydroxyl group pairs (wherein the amino and hydroxyl groups may or may not be vicinal and may or may not be on chiral centers) can be formed and, moreover, can be formed in an organic solvent with a minimal quantity of divalent transition metal ion (e.g. copper (II) ion) without having to use ammonium hydroxide to form a transition metal ammonium ion (e.g. cupraammonium ion). By our invention we have also discovered that the polyaminoorganic compound-transition metal salt complexes of this invention will survive under acylating reaction conditions which transform a free amino group to an N-acylated derivative thereof and, furthermore, that the transition metal salt complexes of this invention will prevent the complexed amino/hydroxyl groups from entering into the reaction. Also, we have discovered that a divalant transition metal complex of this invention (e.g. a copper (II) complex) can be decomplexed by release of the transition metal cation (e.g. a copper (II) cation) and that the polyamino-organic compound can be recovered intact. By our invention, therefore, we have discovered a novel and simple method for preparing blocked derivatives in situ of amino groups having an available neighboring hydroxyl function not necessarily in the vicinal positions by preparation of a transition metal complex (e.g. a copper (II) complex) thereof which, after reaction of the complexed molecule with an acylating reagent whereby N-acyl derivatives of non-complexed amino functions are prepared, can be converted, by removing the transition metal cation (e.g. a copper (II) cation), to a selectively N-acylated polyamine compound free of divalent transition metal cations, e.g. copper (II).

DESCRIPTION OF THE PROCESS ASPECT OF THE INVENTION

The process sought to be patented resides in the concept of a process for selectively blocking amino groups with an acyl blocking group, Y, in a polyamino-organic compound, at least one of said amino groups having an available neighboring hydroxyl group;

which comprises the reaction of said polyaminoorganic compound in an inert organic solvent, with a salt of a divalent transition metal cation selected from the group consisting of copper (II), nickel (II), cobalt (II), cadmium (II) or with mixtures thereof, whereby is formed a complex of said polyaminoorganic compound between said transition metal salt and said available neighboring amino and hydroxyl group pairs;

followed by the reaction in situ of the resulting polyamino-organic compound-transition metal salt complex with an amine blocking reagent having an acyl blocking group, Y; thence reaction of the resulting polyamino-organic compound-transition metal salt complex having acyl blocking groups, Y, on non-complexed amino groups, with a transition metal precipitating reagent or with ammonium hydroxide, whereby transition metal cation is removed.

In this specification and in the claims the phrases "one of said amino groups having an available neighboring hydroxyl group" and "available neighboring amino and hydroxyl group pairs" include amino and hydroxyl functions which are positioned on adjacent carbon atoms in a cis-vicinal or diequatorial transvicinal manner and also includes amino and hydroxyl groups which are not positioned on vicinal carbons but which are spatially adjacent (i.e. they are close enough to be hydrogen bonded) and available to each other. Further, by the term "available" is meant that, in addition to being available to each other, to be useful in the process of this invention, the neighboring amino and hydroxyl group pairs must be so situated in the polyaminoorganic compound molecule so as to be sterically available to an approaching reagent such as a cation of a divalent transition metal. Thus, for example, in a 4,6-di-O-(aminoglycosyl)-2-deoxystreptamine having a 2'-amino group such as in sisomicin, tobramycin, verdamicin and gentamicins $C_1$, $C_{1a}$ and $C_2$, although in one of the conformers, the 5-hydroxyl group of the 2-deoxystreptamine moiety in neighboring and available to the 2'-amino group, the 5-hydroxyl group is so sterically hindered that a salt of a divalent transition metal such as cupric acetate, cannot get into sufficiently close proximity to the 5-hydroxyl-2'-amino pair to form a transition metal salt complex thereof.

Transition metal salts useful as complexing agents in our process include any divalent salt of copper (II), nickel (II), cobalt (II) and cadmium (II). Among those which have strongest complexing activity are divalent transition metal salts of weak acids, preferably weak organic acids such as benzoic, propionic, and acetic acid. Preferred divalent transition metal salts includes the acetate salt of copper (II), nickel (II), cobalt (II), and cadmium (II) and mixtures thereof. Of particular use are nickel (II) acetate, copper (II) acetate and cobalt (II) acetate.

In the aminocyclitol-aminoglycoside art, we have found divalent transition metal halide salts, particularly cupric chloride, to be useful in improving yields when preparing a 6'-N-acyl derivative of a 4,6-di-O-(aminoglycosyl)-2-deoxystreptamine but that, when a 3,6'-di-N-acyl or 3,2',6'-tri-N-acyl derivative of the same aminoglycoside is desired, better results are obtained when a divalent transition metal acetate, particularly cupric acetate, nickel (II) acetate, cobalt (II) acetate or mixtures thereof, is employed as complexing agent.

When preparing selectively blocked N-acyl derivatives of aminocyclitol-aminoglycosides, divalent transition metal salts of strong inorganic acids, e.g. the sulfate, phosphate and nitrate salts, are less desirable as complexing agents than the corresponding salts of weak organic acids such as the acetate, benzoate and propionate salts.

In our process, in order to obtain strongly bound complexes of the available neighboring amino and hydroxyl group pairs, and thus obtain selectivity when N-acylating the noncomplexed amino groups, it is desirable to use a divalent transition metal salt. When monovalent transition metal salts are used, e.g. cuprous acetate, the cuprous acetate complex of available neighboring hydroxyl and amino group pairs is formed in poor yields and is weakly bound so that when the N-acylation step is carried out, N-acylation occurs at the sites of weakly complexed amino groups (albeit at a somewhat slower rate) as well as at the non-complexed amino group sites resulting in mixtures of products and poorer yields of desired product.

The process of this invention is carried out in an inert organic solvent which includes any organic solvent in which the polyamino-organic compound and transition metal salt as well as the resulting polyamino-organic compound-transition metal salt complex intermediate are reasonably soluble, and which will not react to any great extent with the reagents of this process. Preferred solvents are polar, aprotic organic solvents, particularly dialkylamides (e.g. dimethylformamide) and dialkylsulfoxides (e.g. dimethylsulfoxide). Polar protic solvents such as lower alkanols, particularly methanol and ethanol, may also be used in our process when such solvents are required for solubility reasons. When using protic solvents in our process, it is usually desirable to employ a greater quantity of divalent transition metal salt than when using aprotic solvents since protic solvents weaken the complexed functions in the polyamino-organic compound-transition metal salt complex.

It is preferable to utilize substantially anhydrous solvents in our process in order to obtain maximum yields and maximum complexing stability of the polyamino-organic compound-transition metal salt complex intermediates and, thus, to obtain maximum yield of desired selectively blocked N-acyl derivatives of the non-complexed amines in the polyamino compound. However, water may be present (and is frequently desirable for solubility reasons) even in amounts up to about 25% (by volume) and higher without affecting the yields of selectively blocked N-acylated polyamino product, provided additional divalent transition metal salt is employed since water, being a protic solvent, also weakens the complexed functions in the polyamino-organic compound transition metal salt complex intermediates. When too much water is employed, the polyamino-organic compound-transition metal salt complexes are destroyed to a greater extent so that, when the final N-acylation step is carried out, the amines having available neighboring hydroxyl groups are not sufficiently protected by their transition metal salt complexes and will also react with the acylating reagent as well as the non-complexed amino groups resulting in a mixture of products similar to those obtained when the acylating reaction is carried out in the absence of the polyamino-organic compound-transition metal salt complexes.

Thus, in our process, an equilibrium appears to exist between the polyamino-organic compound having at least one available neighboring amino/hydroxy group pair [A], the transition metal salt (e.g. cupric acetate, Cu(OAc)$_2$) and the solvent which may be indicated as follows:

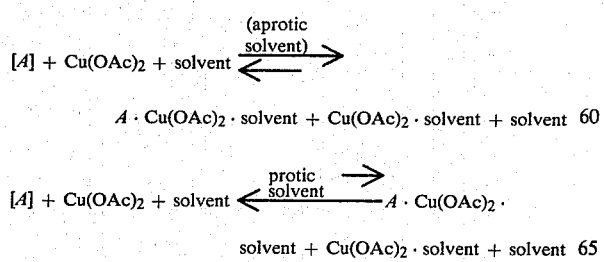

With an aprotic solvent, the equilibrium favors the formation of a transition metal salt complex of a polyamino-organic compound having available, neighboring amino/hydroxyl groups, while an organic protic solvent or the presence of excess water in an organic aprotic solvent favors decomplexing of the polyamino-organic compound transition metal salt complex. Thus, in the latter case, in order to obtain high yields of the polyamino-organic compound-salt complex in solution, greater quantities of transition metal salt are required to force the equilibrium in the desired direction than is necessary when an essentially anhydrous aprotic solvent is used.

Usually, when carrying out the process of this invention, the molar quantity of transition metal salt used in the first step of the process is at least equal to the molar quantity of the polyamino-organic compound times the number of available, neighboring amino- and hydroxyl group pairs therein, and the molar quantity of acylating agent used in the second step of our process is about equal to the molar quantity of the polyamino-organic compound times the number of non-complexed amino functions in the molecule which are to be protected. Whether or not aprotic or protic organic solvents are employed or water is present in the reaction mixture, the molar quantity of N-acylating reagent in the second step of our in situ process always remains about equal to the molar quantity of polyamino-organic compound times the number of non-complexed amino groups which are to be N-acylated.

While the molar quantity of N-acylating reagent is usually equal to the molar quantity of the polyamino-organic compound multiplied by the number of all the non-complexed amines in the molecule, when there exists a difference in the reactivity of the non-complexed amines, one may use less N-acylating reagent if one desires to N-acylate only the more reactive amines. Thus, for example, upon reaction of sisomicin with at least two moles of a transition metal salt (e.g. cupric acetate) in an inert solvent (e.g. dimethylsulfoxide), there is obtained a sisomicin-transition metal salt complex (e.g. sisomicin-cupric acetate complex) wherein the transition metal salt forms a complex with the 3"-amino function-4"-hydroxyl group pair and with the 1-amino-2"-hydroxyl group pair leaving three amino groups non-complexed, i.e. those at the 3, 2' and 6' positions. Reaction of the foregoing in situ with about three mole of N-acylating reagent (e.g. acetic anhydride) followed by removal of the transition metal cation (e.g. copper II) by reaction with hydrogen sulfide yields a tri-N-acyl derivative, e.g. 3,2',6'-tri-N-acetylsisomicin. Alternatively, reaction of the corresponding sisomicin-nickel (II) acetate complex in methanol with only two moles of N-acylating reagent (e.g. N-(2,2,2-trichloroethoxycarbonyloxy)succinimide) yields the 2',6'-di-N-acyl derivative (e.g. 2',6'-di-N-(2,2,2-trichloroethoxycarbonylsisomicin) in excellent yields, the more reactive 2' and 6' amino groups having been preferentially N-acylated over the less reactive 3-amino group under these conditions.

In our process, after the polyamino-organic compound-transition metal salt complex has been reacted with an acylating agent to N-acylate the non-complexed amino groups, the transition metal cation is then conveniently removed from the N-acylated polyamino-organic compound-transition metal salt complex by means of a transition metal precipitating reagent or by means of ammonium hydroxide. In the latter case, the transition metal cation is removed by the preferential formation of a complex with ammonium hydroxide which is soluble in ammonium hydroxide and water. This method of removing the transition metal cation is convenient when the selectively blocked N-acyl polyamino-organic derivative is soluble in organic solvents since it may be then extracted from the aqueous organic solvent mixture which contains the ammonium hydroxide transition metal salt complex.

In carrying out our process, it is usually more convenient to remove the transition metal cation by means of precipitating reagents known in the art. Useful precipitating reagents include dioxime of dimethylglyoxal, 1,3-dicarbonylalkanes such as acetylacetone and heptane-3,5-dione as well as sulfide precipitating reagents such as ammonium sulfide, alkali metal sulfides (e.g. sodium sulfide), alkaline earth metal sulfides (e.g. calcium sulfide), alkaline earth metal hydrosulfides (e.g. sodium hydrosulfide) and hydrogen sulfide. Of the foregoing, particularly useful precipitating reagents are dioxime of dimethylglyoxal, acetylacetone and hydrogen sulfide.

When removing the transition metal cation, hydrogen sulfide is a precipitating reagent of choice since it is a simple procedure to merely bubble hydrogen sulfide through the reaction mixture; also, the resulting transition metal sulfide is completely precipitated in a short period of time and is easily removed by filtration.

The acyl blocking groups, Y, and the corresponding acylating reagents whereby they are formed are well known in the art as well as methods for their removal after a desired chemical transformation has been carried out at some other site in the molecule. In this application and in the claims, acyl blocking groups, Y, which may be selectively introduced in situ onto non-complexed amino functions in a polyamino-organic compound transition metal salt complex intermediate are contemplated as including benzyloxycarbonyl and substituted benzyloxycarbonyl groups such as p-nitrobenzyloxycarbonyl and p-methoxybenzyloxycarbonyl (which are easily removable by catalytic reduction); aryloxycarbonyl groups such as phenoxycarbonyl; and alkoxycarbonyl groups such as methoxycarbonyl, ethoxycarbonyl and the like (which are preferentially removed by basic hydrolysis); trichloroethoxycarbonyl groups (removable by zinc in acetic acid); tertiaryalkoxycarbonyl groups such as tert.-butoxycarbonyl and tert.-amyloxycarbonyl groups (removable by mild acid hydrolysis); halogenoalkylcarbonyl groups such as chloroacetyl (removable with base or with thiourea or a similar reagent) and trifluoroacetyl (easily removed under mild basic conditions); succinimido and phthalimido groups (easily removed by means of hydrazine) and alkanoyl groups such as acetyl, propionyl, and the like as well as aroyl groups such as benzoyl (which are removed by basic hydrolysis). The reaction conditions necessary to introduce any of the foregoing N-acyl derivatives on a free amino function are well documented in the literature and within the knowledge and expertise of one skilled in the art of amine chemistry.

Polyamino-organic compounds useful as starting compounds in our process include any polyamino-organic compound which has at least one amino function which has an available neighboring hydroxyl group and which also has at least one amino function which is either devoid of an available neighboring hydroxyl group and therefore cannot form a complex with a transition metal salt or which is sterically less available to a neighboring hydroxyl so that any salt complex formed at that site would be less stable than other strongly complexed amino/hydroxyl pairs, thus rendering the amino function available to N-acylation in the second step of our process.

The polyamino-organic starting compounds of our process may be substituted by groups other than hydroxyl groups and may contain hetero atoms provided they do not react with transition metal salts or with the acylating reagents. Thus, the polyamino-organic starting compounds of this process are preferably devoid of sulfhydryl and mercaptyl groups.

Contemplated as included among the polyamino-organic starting compounds of our process are monocyclic-, bicyclic- and tricyclic-polyaminoaryl hydroxides such as

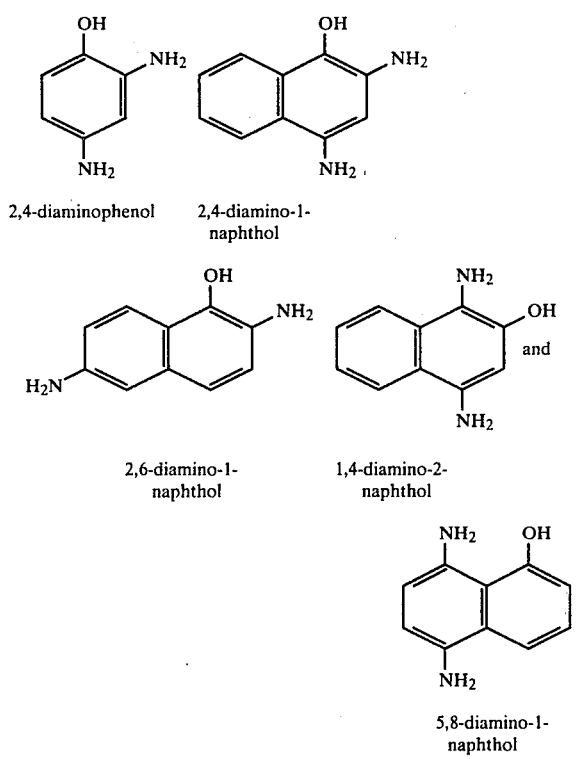

2,4-diaminophenol  2,4-diamino-1-naphthol 2,6-diamino-1-naphthol  1,4-diamino-2-naphthol and 5,8-diamino-1-naphthol as well as polyaminocycloalkanols such as (cis,cis,cis)-2,4-diaminocyclohexanol and (trans,cis,trans)-2,4-diaminocyclohexanol and acyclic polyamino compounds such as 2,6-diaminohexanol.

In acyclic polyamino-organic starting compounds of our process, amino and hydroxyl groups are neighboring and available to each other which are positioned so that the carbon chain (or hetero carbon chain) containing the amino/hydroxyl group pairs can form a five, six, or seven membered ring together with the transition metal cation.

Our process is particularly useful in the carbohydrate art when carrying out chemical transformations of pseudodisaccharides such as 4-O-(6'-amino-6'-deoxyglucosyl)deoxystreptamine, neamine, garamine, kanamine, paromamine, and the gentamines (e.g., $C_1$, $C_{1a}$, $C_2$, $C_{2b}$, etc.).

Our process finds its greatest use, however, in the aminocyclitol-aminoglycoside art where chemical transformations of aminoglycoside antibiotics are continually being made to synthesize new derivatives having enhanced antibacterial activity and/or a more favorable antibacterial spectrum. Most of these transformations are multistep, low yield processes in which several initial steps are directed merely to protecting amino and/or hydroxyl functions with blocking groups prior to carrying out the main chemical transformation step, in an attempt to improve the yield of desired transformation product. By our process, the amino groups which require protection are selectively blocked in excellent yield in a simple two-step-one-vessel procedure.

4,5-Linked aminoglycoside antibiotics containing deoxystreptamine which are useful starting compounds of our process include ribostamycin (in which the 1-amino-6-hydroxyl group pair is converted in situ to a transition metal salt complex, thence all other amino functions are N-acylated followed by removal of the transition metal salt, thence methylation of the resulting 1-N-unsubstituted-poly-N-acylribostamycin utilizing known methylation techniques to produce 1-N-methylribostamycin having antibacterial activity); xylostamycin, 3'-deoxyribostamycin, and 3',4',5''-trideoxyribostamycin. Other useful starting compounds include 4-O-linked-streptamine containing aminocyclitol-aminoglycosides such as 1,3-di-de-N-amidinodihydrostreptomycin which, when reacted with at least two equivalents of cupric acetate, forms in situ a cupric acetate complex involving the 1-amino and 6-hydroxy group pair and the 3-amino and 2-hydroxyl group pair so that, upon reaction with an acylating reagent followed by removal of the cupric cation, a 2''-N-acyl-1,3-di-de-N-amidinodihydrostreptomycin derivative is formed exclusively and in excellent yields. On the other hand, if a transition metal salt is not added to the 1,3-di-de-N-amidinodihydrostreptomycin prior to treatment with an acylating reagent, there is formed a mixture of products of which the 1-N-acyl derivative is predominant.

The preferred mode of our process is that wherein amino groups are selectively blocked in a 4,6-di-O-(aminoglycosyl)-1,3-diaminocyclitol antibacterial agent. By the novel process of this invention, it is now possible to easily prepare in good yields selectively blocked aminoglycoside antibiotic derivatives such as 2',6'-di-N-acyl, 3,6'-di-N-acyl, 3,2',6'-tri-N-acyl, and 1,3,2',6'-tetra-N-acyl derivatives of 4,6-di-O-(aminoglycosyl)-1,3-diaminocyclitol derivatives by a two-step-one-vessel process, all of which were heretofore unknown and which are valuable as intermediates in preparing antibacterially active transformation products of the parent aminoglycoside.

A particularly valuable mode of our process is that whereby is prepared a 3,2',6'-tri-N-acyl derivative of a 4,6-di-O-(aminoglycosyl)-1,3-diaminocyclitol such as sisomicin, tobramycin, verdamicin, gentamicin $C_1$, gentamicin $C_{1a}$ and gentamicin $C_2$, which are valuable intermediates in preparing the corresponding 1-N-alkylaminoglycosides (after removal of the N-acyl groups at the 3, 2' and 6' positions) which are valuable antibacterial agents described in Belgium Patent No. 818,431 and South African Patent No. 74/4939. Of the foregoing, 3,2',6'-tri-N-acylsisomicins, particularly 3,2',6'-tri-N-acetylsisomicin, are of great value as intermediates in preparing 1-N-ethylsisomicin, a potent antibacterial agent having an improved antibacterial spectrum over that of its precursor antibiotic, sisomicin.

In a preferred mode of preparing a 3,2',6'-tri-N-acylaminocyclitol-aminoglycoside (e.g. 3,2',6'-tri-N-acetylsisomicin) by our process, sisomicin is dissolved in an inert solvent (e.g. aqueous dimethylformamide) to which is added a divalent transition metal salt (e.g. cupric acetate hydrate) in an amount equal to about 15 molar equivalents per mole of sisomicin (two molar equivalents being required to form transition metal salt complexes with the 1-amino-2''-hydroxyl group pairs and with the 3''-amino-4''-hydroxyl group pairs and additional excess transition metal salt being required because of the presence of water) and the reaction stirred at room temperature (usually about 30 minutes), thus completing the first step of our two-step in situ process. To the thus prepared solution of aminocyclitol-aminoglycoside-divalent-transition metal salt complex (e.g. sisomicin-cupric acetate complex) is added an acylating reagent (e.g. acetic anhydride) in an amount equal to about three molar equivalents per mole of aminoglycoside derivative (e.g. sisomicin-cupric acetate salt complex) (there being three non-complexed amino groups at positions 3, 2' and 6') and the reaction mixture is stirred at room temperature until the reaction is complete (usually in about 30 minutes) as evidenced by a thin layer chromatogram. The transition metal cation (e.g. copper II) is then easily removed by bubbling hydrogen sulfide through the reaction mixture followed by separation of the resulting precipitate of the sulfide salt of the transition metal (e.g. cupric sulfide) by filtration to obtain a filtrate comprising the 3,2',6'-tri-N-acyl-aminocyclitol-aminoglycoside (e.g. 3,2',6'-tri-N-acetylsisomicin) which may be used without isolation or purification as intermediates to prepare the corresponding 1-N-substituted derivatives, specifically the corresponding 1-N-alkyl derivatives utilizing procedures such as described in South African Patent No. 74/4939 and in copending U.S. Ser. No. 492,998 filed July 30, 1974 of common assignee as the instant application, now U.S. Pat. No. 4,002,742 the subject matter of which is incorporated herein by reference. Alternatively, the 3,2',6'-tri-N-acyl derivative may be purified and isolated utilizing conventional techniques such as evaporating the solvent and chromatographing a solution of the resultant residue on a column of silica gel.

In carrying out our process, we have found that mixtures of transition metal salt complexes are sometimes advantageously employed to produce good yields of selectively N-acylated polyamino compounds. It is believed this is due to the fact that some transition metal salts form more strongly bound transition metal salt complexes with certain available, neighboring amino/hydroxyl group pairs than do other transition metal salts. Thus, when preparing 3,2',6'-tri-N-acetylsisomicin improved yields are obtained when the aforedescribed process is carried out in an aprotic solvent (e.g. dimethylsulfoxide) utilizing as divalent transition metal salt an equimolar mixture of nickel (II) acetate and cupric acetate (the total molar equivalents of transition metal salts being four times that of sisomicin) followed by reaction in situ of the sisomicin-nickel (II) acetate-cupric acetate complex thereby formed with about three molar equivalents of acetic anhydride per mole of sisomicin, thence removal of the cupric and nickel (II) ions by precipitation as the sulfide salts and thence isolation and purification of the resulting 3,2',6'-tri-N-acetylsisomicin in yields of at least 90% theory as compared with a 76% theoretical yield when cupric acetate was used alone.

A particularly valuable mode of our process is that utilizing cobalt (II) acetate as transition metal whereby is obtained almost theoretical yields of essentially pure selectively blocked N-acylated derivatives. For example, treatment of sisomicin with about two equivalents of cobalt (II) acetate in an aprotic solvent such as dimethylsulfoxide or dimethylformamide followed by treatment in situ of the resulting sisomicin.di-cobalt (II) acetate complex thereby formed with about three equivalents of acetic anhydride followed by removal of the cobalt ion from the tri-N-acetylsisomicin.di-cobalt (II) acetate complex by treatment with hydrogen sulfide, thence isolation of the selectively blocked sisomicin thereby formed yields 3,2',6'-tri-N-acetylsisomicin of high purity in near quantitative yields.

In contrast to the foregoing, prior art acylation procedures utilizing three moles of acetic anhydride per mole of sisomicin without the use of cupric (II), nickel (II) or cobalt (II) ion complexes, produce a mixture of products containing penta-N-acetylsisomicin, mixtures of tetra-N-acetylsisomicins, mixtures of tri-N-acetylsisomicins along with other products from which the desired 3,2',6'-tri-N-acetylsisomicin could not be isolated free from co-produced products.

In the above procedure, by modifying the quantity of transition metal salt and acylating reagent and (incidentally) changing the solvent, one can obtain good yields of 1,3,2',6'-tetra-N-acetylsisomicin instead of 3,2',6'-tri-N-acetylsisomicin. Thus, by adding from about a half to an equimolar equivalent amount of divalent transition metal salt (e.g. cupric acetate hydrate) per mole of sisomicin in an aqueous methanolic solution, there is obtained in situ a sisomicin-cupric acetate complex involving the 3''-amino-4''-hydroxyl group pair. Reaction of the foregoing in situ with about 4 molar equivalents of acetic anhydride followed by removal of the cupric cation by precipitation as the sulfide salt and thence isolation and purification utilizing known techniques yields 1,3,2',6'-tetra-N-acetylsisomicin in yields of almost 80% theory, an intermediate useful when transformation at the 3''-amino group is desired. Without the presence of cupric (II), nickel (II) or cobalt (II) ion in the reaction mixture, the foregoing reaction will produce much lower yields of the product.

In our process, after preparation of the polyaminoorganic compound-transition metal salt complex, one can prepare stepwise in situ mixed N-acyl derivatives of the remaining noncomplexed amino groups when said amines have different degrees of reactivity without having to isolate the first N-acyl derivative prior to preparation of the desired mixed N-acyl derivative. Depending upon the types of N-acyl groups introduced into the molecule and their relative ease of removal, it is possible, by our process, to prepare any desired combination of selectively N-acylated polyamino-organic compound. Thus, for example, by modifying the procedure described hereinabove for the preparation of 3,2',6'-tri-N-acetylsisomicin, it is possible to prepare other selectively N-acylated derivatives thereof such as 1,2',3-tri-N-acetylsisomicin or 2',3-di-N-acetylsisomicin.

Specifically, upon reaction of sisomicin in 95% aqueous methanol with about an equimolar amount of cupric acetate, there is obtained in situ a sisomicin-cupric acetate complex essentially involving the 3''-amino and 4''-hydroxyl groups. Reaction of the foregoing sisomicin-cupric acetate complex with about a molar equivalent of ethylthiotrifluoro acetate produces a monoacyl derivative of the most reactive non-complexed amino function therein; namely, the 6'-amino, to produce in situ 6'-N-trifluoroacetylsisomicin-cupric acetate complex. By subsequently adding about three molar equivalents of acetic anhydride to the foregoing derivative in situ, the remaining three non-complexed amino groups are N-acetylated to produce 1,3,2'-tri-N-acetyl-6'-N-trifluoroacetylsisomicin-cupric acetate complex. After destroying the cupric acetate complex by bubbling hydrogen sulfide through the reaction mixture and separating the resulting cupric sulfide by filtration, evaporation of the filtrate followed by treatment of the residue containing 1,3,2'-tri-N-acetyl-6'-N-trifluoroacetylsisomicin with ammonium hydroxide causes hydrolysis of the 6'-N-trifluoroacetyl group without disturbing the N-acetyl groups. Isolation of the resulting 1,3,2'-tri-N-acetylsisomicin is easily effected by known techniques such as evaporating the solution and chromatographing the resultant residue. The 1,3,2'-tri-N-acylaminoglycosides are valuable intermediates in preparing 6'-N-alkylaminoglycosides, useful antibacterial agents such as those described in co-pending applications of common assignee, Ser. No. 596,799 filed July 17, 1975, now U.S. Pat. No. 4,063,015 and Ser. No. 666,715 filed Mar. 15, 1976 now U.S. Pat. No. 4,044,123.

Additionally, by forming in situ 6'-N-trifluoroacetylsisomicin-cupric acetate nickel (II) acetate complex in dimethylsulfoxide and adding two equivalents of acetic anhydride, there is formed a di-N-acetyl derivative involving the two more reactive non-complexed amino functions at the 3- and 2'-positions to produce in situ 3,2'-di-N-acetyl-6'-N-trifluoroacetylsisomicin-cupric acetate complex, which, after removal of the complex with hydrogen sulfide and hydrolysis of the 6'-N-trifluoroacetyl group by means of mild basic hydrolysis, yields 3,2'-di-N-acetylsisomicin. The 3,2'-di-N-acetylaminocyclitol-aminoglycosides such as 3,2'-di-N-acetylsisomicin are valuable intermediates in the preparation of 1,6'-di-N-alkylaminoglycosides, e.g. 1,6'-di-N-ethylsisomicin, valuable antibacterial agents described in co-pending application of common assignee, Ser. No. 628,637 filed Nov. 4, 1975, now abandoned.

In yet another mode of our process, mixed N-acyl derivatives of a polyamino-organic compound may be prepared by introducing, in situ, some N-acyl derivatives on the polyaminoorganic compound-transition metal salt complex, then destroying the complex (such as with hydrogen sulfide or ammonium hydroxide) followed by N-acylation of the amino functions which formerly had been rendered inactive due to the presence of the complexes. By utilizing this procedure, it is possible to obtain a 1,3,3''-tri-N-acetylsisomicin derivative, a useful intermediate for the preparation of 2',6'-di-N-substituted derivatives such as 2',6'-di-N-alkylsisomicin having antibacterial activity. Thus, for example, treatment of sisomicin with about 2 to 3 molar equivalents of nickel (II) acetate in methanol yields in situ a sisomicin-nickel (II) acetate complex involving the 3''-amino-4''-hydroxyl group pair and the 1-amino-2''-hydroxy group pair. Reaction of the sisomicin-nickel (II) acetate complex in situ with about two moles of N-tert.-butoxycarbonyloxyphthalimide produces a di-N-acyl derivative involving the more reactive non-complexed 2' and 6'-amino groups as compared with the non-complexed 3-amino group to produce 2',6'-di-N-tert.-butoxycarbonylsisomicin-nickel (II) acetate complex. Removal of the nickel (II) ion as nickel sulfide according to our process followed by reaction in situ of the resulting filtrate containing 2',6'-di-N-tert.-butoxycarbonylsisomicin with acetic anhydride yields 1,3,3''-tri-N-acetyl-2',6'-di-N-tert.-butoxycarbonylsisomicin which, upon controlled acid hydrolysis in situ such as by 5% trifluoroacetic acid in tetrahydrofuran yields 1,3,3''-tri-N-acetylsisomicin.

Alternatively, the 2',6'-di-N-tert.-butoxycarbonylsisomicin intermediate prepared by the above procedure may be isolated per se, then reduced with lithium aluminum hydride in tetrahydrofuran to produce 2',6'-di-N-methylsisomicin (i.e. 2'-N-methyl-Antibiotic G-52) useful as antibacterial agent.

The above discussion describing the preparation of selectively N-acylated sisomicin derivatives, particularly valuable intermediates prepared by our novel process, illustrates the flexibility and versatility of our process. Other particularly valuable intermediates prepared by our process are the 6'-N-acyl and 3,6'-di-N-acyl derivatives of aminocyclitol-aminoglycosides such as gentamicin B, gentamicin B$_1$ and kanamycin A, which are also useful intermediates in the preparation of 1-N-substituted derivatives, particularly the 1-N-($\gamma$-amino-$\alpha$-hydroxybutyryl)- and the 1-N-($\beta$-amino-$\alpha$-hydroxypropionyl)- and the 1-N-($\delta$-amino-$\alpha$-hydroxyvaleryl)- derivatives of gentamicins B and B$_1$ and of kanamycin A, all of which are valuable antibacterial agents.

It is to be noted that the foregoing 1-N-(aminohydroxyalkanoyl)aminocyclitol-aminoglycosides may be in the R,S- form or in the R- form or in the S-form. In accordance with this invention, each of the foregoing names includes all three forms. Thus, for example, the name 1-N-($\gamma$-amino-$\alpha$-hydroxybutyryl)gentamicin B includes 1-N-(S-$\gamma$-amino-$\alpha$-hydroxybutyryl)gentamicin B, 1-N-(R-$\gamma$-amino-$\alpha$-hydroxybutyryl)gentamicin B and 1-N-(R,S-$\gamma$-amino-$\alpha$-hydroxybutyryl)gentamicin B and the name 1-N-($\beta$-amino-$\alpha$-hydroxypropionyl)gentamicin B includes 1-N-(S-$\beta$-amino-$\alpha$-hydroxypropionyl)gentamicin B, 1-N-(R-$\beta$-amino-$\alpha$-hydroxypropionyl)gentamicin B, and 1-N-(R,S-$\beta$-amino-$\alpha$-hydroxypropionyl)gentamicin B.

By means of the novel 3,6'-di-N-acyl derivatives of gentamicins B and B$_1$, and of kanamycin A, prepared via the transition metal complexes by the process of this invention, each of gentamicins B and B$_1$ and kanamycin A can now be converted to the corresponding 1-N-aminohydroxyalkanoyl derivatives in high yields of pure product. Thus, for example, kanamycin A is convertible to 3,6'-di-N-benzyloxycarbonylkanamycin A via the dinickel (II) acetate complex in dimethylsulfoxide in over 80% theoretical yield. Reaction of the foregoing 3,6'-di-N-acyl derivative with N-(S-$\gamma$-benzyloxycarbonylamino-$\alpha$-hydroxybutyryloxy)succinimide followed by treatment of the resulting 1-N-(S-$\gamma$-benzyloxycarbonylamino-$\alpha$-hydroxybutyryl)-3,6'-di-N-benzyloxycarbonylkanamycin A with hydrogen and a catalyst to remove the benzyloxycarbonyl protecting groups produces 1-N-(S-$\gamma$-amino-$\alpha$-hydroxybutyryl)-kanamycin A (also known as amikacin and as Antibiotic BB-K-8) of high purity in excellent overall yields of over 50%.

The foregoing process of this invention thus represents a great improvement over the prior art methods of converting kanamycin A to amikacin such as that disclosed in J. Antibiotics 25, 695–708 (1972) whereby kanamycin A is first converted to the 6'-N-benzyloxycarbonyl derivative in 45% yields which, when taken through essentially the same conversions described hereinabove produces purified amikacin in overall yields of less than 10%. Similarly, by the method of our invention, kanamycin A via the 3,6'-di-N-benzyloxycarbonyl intermediate is convertible to 1-N-($\beta$-amino-$\alpha$-hydroxypropionyl)kanamycin A (also known as 1-N-isoserylkanamycin A) in overall yields greater than 50% theory as compared with overall yields of less than 8% via prior art methods utilizing the 6'-N-tert.-butoxycarbonyl intermediate such as described in U.S. Pat. No. 3,939,143.

Similarly, by reacting gentamicin B in dimethylsulfoxide with about 3 molar equivalents of cupric acetate there is obtained in situ the corresponding gentamicin B-cupric acetate complex involving the 3''-amino-4''-hydroxyl and the 1-amino-2''-hydroxyl group pairs. Reaction of the foregoing in situ with about 1 molar equivalent of N-tert.-butoxycarbonyloxyphthalimide yields the corresponding 6'-N-tert.-butoxycarbonylgentamicin B-di-cupric acetate complex, while reaction with at least two moles of the N-tert.-butoxycarbonyloxyphthalimide yields the corresponding 3,6'-di-N-tert.-butoxycarbonylgentamicin B-di-cupric acetate complex. Reaction of each of the foregoing with hydrogen sulfide followed by separation of the resulting cupric sulfide by filtration yields a solution comprising 6'-N-tert.-butoxycarbonylgentamicin B or 3,6'-di-N-tert.-butoxycarbonylgentamicin B, respectively. Each of the foregoing may be isolated from their respective reaction solutions and purified in known manner and thence reacted with N-(S-$\gamma$-benzyloxycarbonylamino-$\alpha$-hydroxybutyryloxy)succinimide or with N-(S-$\beta$-benzyloxycarbonylamino-$\alpha$-hydroxypropionyloxy)succinimide or with N-(S-$\delta$-amino-$\alpha$-hydroxyvaleryl)succinimide according to procedures such as described in the Examples and in the prior art to obtain 1-N-(S-$\gamma$-amino-$\alpha$-hydroxybutyryl)gentamicin B, or 1-N-(S-$\beta$-amino-$\alpha$-hydroxypropionyl)-gentamicin B, or 1-N-(S-$\delta$-amino-$\alpha$-hydroxyvaleryl)gentamicin B, respectively, all of which are valuable antibacterial agents.

Alternatively, one may carry out the chemical conversion at C-1 in situ without isolating the 3,6'-di-N-tert.-butoxycarbonylgentamicin B to obtain the corresponding 1-N-(S-$\gamma$-amino-$\alpha$-hydroxybutyryl)gentamicin B or 1-N-(S-$\beta$-amino-$\alpha$-hydroxypropionyl)gentamicin B or 1-N-(S-$\delta$-amino-$\alpha$-hydroxyvaleryl)gentamicin B in excellent overall yields of about 50% theory. The foregoing also represents a significant improvement over prior art methods for preparing these compounds such as described by P. J. L. Daniels et al in J. Antibiotics 27, 889 (1974) which produce said 1-N-aminohydroxyalkanoylgentamicin C$_1$ derivatives in less than 15% yields.

It is to be noted, also, that by our process the yield of 6'-N-tert.-butoxycarbonylgentamicin B is nearly quantitative and requires no chromatographic purification in contrast to prior art procedures which give only about 46% yields and requires chromatographic isolation.

By our invention we have also discovered that, when using our novel 3,6'-di-N-acyl-gentamicin B intermediates, e.g. 3,6'-di-N-benzyloxycarbonylgentamicin B, in the conversion of gentamicin B to a 1-N-(aminohydroxyalkanoyl) derivative thereof, e.g. 1-N-($\beta$-amino-$\alpha$-hydroxypropionyl)gentamicin B, reaction of the 3,6'-di-N-acyl derivative with a racemic reagent, e.g. N-($\beta$-benzyloxycarbonylamino-$\alpha$-hydroxypropionyloxy)succinimide will yield a 3,6'-di-N-acyl-1-N-(R,S-aminohydroxyalkanoyl)gentamicin B diastereoisomeric mixture (e.g. 3,6'-di-N-(benzyloxycarbonyl)-1-N-(R,S-$\beta$-benzyloxycarbonylamino-$\alpha$-hydroxypropionyl)gentamicin B) which, surprisingly, is easily separated via chromatographic techniques into each diastereoisomer, e.g. into 3,6'-di-N-benzyloxycarbonyl-1-N-(R-$\beta$-benzyloxycarbonylamino-$\alpha$-hydroxypropionyl)gentamicin B and 3,6'-di-N-(benzyloxycarbonyl)-1-N-(S-$\beta$-benzyloxycarbonylamino-$\alpha$-hydroxypropionyl)gentamicin B which, upon removal of the 3,6'-di-N- blocking groups yields the respective diastereoisomeric antibacterial agent, e.g. 1-N-(R-$\beta$-amino-$\alpha$-hydroxypropionyl)gentamicin B and 1-N-(S-$\beta$-amino-$\alpha$-hydroxypropionyl)gentamicin B, respectively. Alternatively, removal of the protecting groups from 3,6'-di-N-(benzyloxycarbonyl)-1-N-(R,S-$\beta$-benzyloxycarbonylamino-$\alpha$-hydroxypropionyl)gentamicin B yields 1-N-(R,S-$\beta$-amino-$\alpha$-hydroxypropionyl)gentamicin B which can be obtained pure from impurities by chromatography on silica gel but which is not thereby separated into the respective diastereoisomers. Thus, by means of our novel 3,6'-di-N-acyl intermediates, it is possible to produce both diastereoisomeric derivatives of a 1-N-(aminohydroxyalkanoyl)gentamicin B using a racemic reagent whereas heretofore, in order to obtain a given diastereoisomeric derivative, it was necessary to utilize the corresponding reagent enantiomer.

Described above are some prefered modes of carrying out the process of our invention, specific illustrations of which are more fully described in the Examples. Equivalents thereof will become readily apparent to one skilled in the art from the instant disclosure, said equivalents being considered as part of Applicants' invention which is not to be construed as limited to the specific illustrations described herein and in the Examples.

DESCRIPTION OF THE COMPOSITION-OF-MATTER ASPECTS OF THE INVENTION

Included within the composition-of-matter aspects of this invention are novel selectively blocked aminocyclitolaminoglycoside derivatives which are prepared by our process involving the in situ complexing of neighboring available amino/hydroxyl group pairs with transition metal salts. As discussed hereinabove, the selectively blocked N-acyl derivatives of this invention are valuable intermediates in the preparation of antibacterially active derivatives of said aminocyclitol-aminoglycosides.

One of the composition-of-matter aspects of this invention resides in the concept of A 3,2',6'-tri-N-acyl-4,6-di-O-(aminoglycosyl)-1,3-diaminocyclitol selected from the group consisting of
3,2',6'-tri-N-Y-sisomicin, 3,2',6'-tri-N-Y-verdamicin,
3,2',6'-tri-N-Y-tobramycin, 3,2',6'-tri-N-Y-gentamicin $C_1$,
3,2',6'-tri-N-Y-gentamicin $C_{1a}$, 3,2',6'-tri-N-Y-gentamicin $C_2$,
3,2',6'-tri-N-Y-gentamicin $C_{2a}$, 3,2',6'-tri-N-Y-gentamicin $C_{2b}$,
3,2',6'-tri-N-Y-Antibiotic 66-40B,
3,2',6'-tri-N-Y-Antibiotic 66-40D,
3,2',6'-tri-N-Y-Antibiotic JI-20A,
3,2',6'-tri-N-Y-Antibiotic JI-20B,
3,2',6'-tri-N-Y-Antibiotic G-52,
The 5-epi-, 5-deoxy-, and 5-epi-azido-5-deoxy analogs of the foregoing;
3,2',6'-tri-N-Y-kanamycin B,
3,2',6'-tri-N-Y-3',4'-dideoxykanamycin B,
3,2',6'-tri-N-Y-nebramycin factor 4,
3,2',6'-tri-N-Y-nebramycin factor 5',
3,2',6'-tri-N-Y-3',4'-dideoxy-3',4'-dehydrokanamycin B, and
3,2',6'-tri-N-Y-3',4'-dideoxy-6'-N-methylkanamycin B;

wherein Y is an acyl group, including acyl functions described hereinabove.

The foregoing derivatives are particularly valuable as intermediates in the preparation of the corresponding 1-N-alkyl derivatives thereof which, after removal of the 3,2',6'-tri-N-acyl blocking groups are potent antibacterial agents as described in South African Patent No. 73/9409, and in U.S. application Ser. No. 492,998 filed July 30, 1974 of common assignee, now U.S. Pat. No. 4,002,742. In brief, as illustrated in Examples 16 and 17 by reacting an acid addition salt of the 3,2',6'-tri-N-acyl-4,6-di-O-(aminoglycosyl)-1,3-diaminocyclitols of this invntion with an aldehyde followed by reduction in situ of the resulting Schiff-base derivative at C-1 by procedures analogous to those described in U.S. Ser. No. 492,998 filed July 30, 1974, now U.S. Pat. No. 4,002,742 there is obtained the corresponding 1-N-alkyl-3,2',6'-tri-N-acyl-4,6-di-O-(aminoglycosyl)-1,3-diaminocyclitol which, after removal of the N-acyl derivatives results in much greater overall yields (e.g. usually above 50% theory) of purer 1-N-alkylaminoglycosides than obtained by presently known methods of preparing 1-N-alkylaminoglycosides (usually less than 20% theory).

For example, when preparing 1-N-ethylsisomicin by first converting sisomicin to 3,2',6'-tri-N-acetylsisomicin via the transition metal salt complex in situ process of this invention followed by reaction of a sulfuric acid addition salt of the resulting 3,2',6'-tri-N-acetylsisomicin with acetaldehyde followed by reduction with sodium cyanoborohydride, thence removal of 3,2',6'-tri-N-acetyl functions via basic hydrolysis, there is obtained 1-N-ethylsisomicin of high purity in yields of about 60% theory; whereas conversion of sisomicin to 1-N-ethylsisomicin by the same process but without acetylating at the 3, 2' and 6' positions produces 1-N-ethylsisomicin in yields of about 11% theory. Thus, of particular value in preparing 1-N-alkylaminocyclitolaminoglycoside derivatives are the 3,2',6'-tri-N-acylaminoglycosides wherein the "acyl" is lower alkanoyl, preferably acetyl. Of these, a particularly preferred species is 3,2',6'-tri-N-acetylsisomicin, valuable intermediate in the preparation of 1-N-ethylsisomicin.

Other valuable 3,2',6'-tri-N-acylaminocyclitol-aminoglycosides are those wherein Y is p-methoxybenzyloxycarbonyl or 2,2,2-trichloroethoxycarbonyl, a particularly preferred species being 3,2',6'-tri-N-(2,2,2-trichloroethoxycarbonyl)sisomicin and 3,2',6'-tri-N-(p-methoxybenzyloxycarbonyl)sisomicin, valuable intermediates in the preparation of 1-N-acyl-4,6-di-O-(aminoglycosyl)-1,3-diaminocyclitols, particularly 1-N-acyl derivatives of sisomicin, e.g., 1-N-acetylsisomicin, valuable as antibacterial agents and as intermediates in preparing the corresponding 1-N-alkyl derivatives, said 1-N-acyl derivatives being described in copending applications of common assignee of the instant application, i.e., U.S. Ser. No. 452,586 now U.S. Pat. No. 4,029,882 and Ser. No 452,751, now abandoned both filed Mar. 19, 1974.

Another composition-of-matter aspect of this invention is the concept of a 2',6'-di-N-Y-4,6-di-O-(aminoglycosyl)-1,3-diaminocyclitol selected from the group consisting of
2',6'-di-N-Y-sisomicin, 2',6'-di-N-Y-tobramycin,
2',6'-di-N-Y-gentamicin $C_{1a}$, 2',6'-di-N-Y-Antibiotic 66-40B,
2',6'-di-N-Y-Antibiotic 66-40D,
2',6'-di-N-Y-Antibiotic JI-20A, the 5-epi-, 5-deoxy-, and 5-epi-azido-5-deoxy analogs of the foregoing;

2',6'-di-N-Y-kanamycin B,

2',6'-di-N-Y-3',4'-dideoxykanamycin B, and

2',6'-di-N-Y-3',4'-dideoxy-3',4'-dehydrokanamycin B;

wherein Y is an acyl group.

Particularly valuable derivatives of the foregoing are those wherein Y is 2,2,2-trichloroethoxycarbonyl, tert.-butoxycarbonyl, or p-methoxybenzyloxycarbonyl, particularly 2',6'-di-N-(2,2,2-trichloroethoxycarbonyl)-sisomicin, 2',6'-di-N-(tert.-butoxycarbonyl)sisomicin, and 2',6'-di-N-(p-methoxybenzyloxycarbonyl)sisomicin, valuable intermediates in preparing 2',6'-di-N-alkyl-4,6-di-O-(aminoglycosyl)-1,3-diaminocyclitols having antibacterial activity, e.g., 2',6'-di-N-ethylsisomicin.

Still another composition-of-matter aspect of this invention resides in the concept of a 3,6'-di-N-acyl-4,6-di-O-(aminoglycosyl)-1,3-diaminocyclitol selected from the group consisting of 3,6'-di-N-Y-kanamycin A, 3,6'-di-N-Y-gentamicin B, 3,6'-di-N-Y-gentamicin B$_1$, 3,6'-di-N-Y-gentamicin A$_3$, 3,6'-di-N-Y-6'-N-methylkanamycin A wherein Y is an acyl group. Particularly preferred compounds of this aspect of the invention are those wherein Y is a member selected from the group consisting of acetyl, tert.-butoxycarbonyl, p-methoxybenzyloxycarbonyl, benzyloxycarbonyl and 2,2,2-trichloroethoxycarbonyl. When Y is acetyl, the foregoing derivatives are valuable mainly as intermediates in the preparation of the corresponding 1-N-alkyl derivatives via the procedure described hereinabove and in Example 18B. When Y is such as tert.-butoxycarbonyl, p-methoxybenzyloxycarbonyl, benzyloxycarbonyl and 2,2,2-trichloroethoxycarbonyl, the foregoing compounds are of particular value in the preparation of the corresponding 1-N-alkyl and 1-N-($\gamma$-amino-$\alpha$-hydroxybutyryl), 1N-($\beta$-amino-$\alpha$hydroxypropionyl) and 1-N-($\gamma$-amino-$\alpha$-hydroxyvaleryl) derivatives (as discussed in the Description of the Process Aspect of the Invention) which, when the 3,6'-di-N-acyl groups are removed, are potent antibacterial agents known in the art.

Still another composition-of-matter aspect of our invention resides in the concept of a polyamino-organic compound-transition metal salt complex wherein at least one of said amino groups has an available neighboring hydroxyl group and said salt is a salt of a divalent transition metal cation selected from the group consisting of copper (II), nickel (II), cobalt (II), and cadmium (II) or is a mixture of said salts, said polyamino-organic compound-transition metal salt complex having complex functions between said divalent transition metal salt and said available neighboring amino and hydroxyl group pairs, the number of complex functions being no greater than the number of said available neighboring amino and hydroxyl group pairs.

Usually, all the complex functions are the same in the polyamino-organic compound-transition metal salt complexes of this invention; however, a polyamino-organic compound-transition metal salt complex may contain different complex functions, e.g. as in sisomicin-cupric acetate-nickel (II) acetate complex discussed hereinabove and specifically described in the Examples.

The polyamino-organic compound-transition metal salt complexes are conveniently used as intermediates in situ in the solvent medium in which they are prepared, and therefore, there is usally no need to isolate the transition metal salt complexes of this invention. Thus, another aspect of our invention resides in the concept of a composition comprising a polyamino-organic compound-transition metal salt complex and an inert, organic solvent, particularly compositions comprising an aminocyclitol-aminoglycoside-transition metal salt complex and an inert organic solvent. As disclosed hereinabove in the *Process Aspect of the Invention*, the compositions of this invention may also contain water and still be useful in carrying out the process of this invention. The transition metal salt complexes can be isolated, however, either by evaporating the solvent medium in vacuo or by precipitating the complex by pouring the solution thereof into ethyl acetate, whereby is produced a polyamino-organic compound-transition metal salt complex as an amorphous powder which is characterized by colors different from the transition metal salt and of the polyamino-organic compound precursor, and which are also characterized by infrared spectrum taken in the solid state. Furthermore, in solutions, the spectrum of the isolated transition metal salt complexes of the polyamino-organic compound in the visible region is different from that of either the transition metal salt alone or the polyamino-organic compound alone.

The isolated transition metal salt complexes of antibacterial polyamino-hydroxy compounds per se usually exhibit an antibacterial activity in vitro similar to that of their uncomplexed precursors. In the case of transition-metal salt complexes of 4,6-di-O-(aminoglycosyl)-2-deoxystreptamines, e.g., gentamicin B-dicobalt (II) acetate complex, the onset of antibacterial activity is usually slower than that of the parent uncomplexed precursor.

Preferred transition metal salt complexes of this invention are those derived from cupric acetate, nickel (II) acetate, cobalt (II) acetate or mixtures thereof, particularly those wherein the polyamino-organic compound is an aminocyclitol-aminoglycoside, preferably a 4,6-di-O-(aminoglycosyl)-1,3-diaminocyclitol such as those specifically described in the Examples.

Of particular value are the transition metal salt complexes of 4,6-di-O-(aminoglycosyl)-2-deoxystreptamines such as tobramycin, sisomicin, verdamicin, gentamicin C$_1$, gentamicin C$_{1a}$, gentamicin B, gentamicin B$_1$, and kanamycin A, which contain available neighboring amino functions and hydroxyl group pairs at the 3'' and 4''-positions and at the 1 and 2''-positions, respectively. When the transition metal salt complexes of the foregoing aminocyclitol-aminoglycosides are prepared with at least 2 moles of transition metal salt per mole of 4,6-di-O-(aminoglycosyl)-1,3-diaminocyclitol there will be complex functions involving the transition metal salt and both neighboring amino group/hydroxyl group pairs. Alternatively, reaction of any of the aforementioned 4,6-di-O-(aminoglycosyl)-1,3-diaminocyclitols with but one molar equivalent of transition metal salt will produce a polyamino-organic compound-transition metal salt complex of this invention having but one complex function which is believed to be at the site of the 3''-methylamino-4''-hydroxyl group pair. As discussed in detail hereinabove and as exemplified in the Examples, each polyamino-organic compound-transition metal salt complex is useful for preparing different selectively blocked derivatives of the parent aminoglycoside. Thus, 4,6-di-O-(aminoglycosyl)-1,3-diaminocyclitols having two complexing functions, e.g. sisomicin-dicupric acetate complex, upon reaction with three moles of acylating reagent according to our process will produce high yields of a 3,2',6'-tri-N-acylsisomicin; whereas a 4,6-di-O-(aminoglycosyl)-1,3-diaminocyclitol having but one complexing function therein (e.g. sisomicin-mono-cupric acetate complex) upon reaction with four moles of acylating reagent will produce almost theoretical yields of 1,3,2',6'-tetra-N-acylsisomicin.

Included among the preferred polyamino-organic compound-transition metal salt complexes of this invention are sisomicin-dicupric acetate complex, sisomicin-dicobalt (II) acetate complex, sisomicin-dinickel (II) acetate complex and the mixed sisomicin-cupric acetate-nickel (II) acetate complex, all of which are valuable intermediates in preparing 3,2',6'-tri-N-acylsisomicin selectively blocked compounds which, in turn, are valuable intermediates in the preparation of 1-N-alkylsisomicins (particularly 1-N-ethylsisomicin) and 1-N-acylsisomicin (particularly 1-N-acetylsisomicin) valuable antibacterial agents.

Other particularly valuable polyamino-organic compound-transition metal salt complexes of this invention are gentamicin B-dicupric acetate complex and kanamycin A-dinickel (II) acetate complex, valuable intermediates in preparing the 3,6'-di-N-acyl derivatives of gentamicin B and kanamycin A, e.g. 3,6'-di-N-tert.-butoxycarbonylgentamicin B and 3,6'-di-N-benzyloxycarbonylkanamycin A, in turn, valuable intermediates in preparing the 1-N-($\beta$-amino-$\alpha$-hydroxypropionyl)-, the 1-N-($\gamma$-amino-$\alpha$-hydroxybutyryl)-, and the 1-N-($\gamma$-amino-$\alpha$-hydroxyvaleryl)- derivatives of gentamicin B and of kanamycin A and their reduced analogs, valuable antibacterial agents.

DESCRIPTION OF THE PROCESS IMPROVEMENT ASPECT OF THE INVENTION

Another aspect of our invention resides in the concept of process improvements which result when novel selectively blocked aminocyclitol-aminoglycosides of this invention are utilized as intermediates in processes known in the art. Particularly valuable process improvements include the improvement resulting from the use of 3,2',6'-tri-N-acetylsisomicin as starting compound in the process described in U.S. Ser. No. 492,998 filed July 30, 1974, now U.S. Pat. No. 4,002,742, whereby 1-N-ethylsisomicin is prepared. Another particularly valuable process improvement aspect of this invention is the improvement resulting from the use of 3,6'-di-N-acyl derivatives of kanamycin A and of gentamicins B and B$_1$, in particular 3,6'-di-N-tert.-butoxycarbonyl or the 3,6'-di-N-benzyloxycarbonyl, 3,6'-di-N-p-methoxybenzyloxycarbonyl, and the 3,6'-di-N-(2,2,2-trichloroethoxycarbonyl) derivatives thereof as starting compounds in known processes for preparing the 1-N-($\beta$-amino-$\alpha$-hydroxypropionyl)-, the 1-N-($\gamma$-amino-$\alpha$-hydroxybutyryl)-, and the 1-N-($\gamma$-amino-$\alpha$hydroxyvaleryl)- derivatives of kanamycin A and of gentamicins B and B$_1$.

As described in detail under the *Description of the Composition-of-Matter Aspect of the Invention* and in the Examples, by using novel, selectively blocked N-acyl derivatives of our invention, greatly improved yields of purer 1-N-substituted aminoglycosides are obtained in fewer reaction steps than by known, prior art methods. These process improvements, resulting from the use of the aminocyclitol-aminoglycoside transition-metal salt complexes, are part of our overall inventive concept and are specifically defined in the claims attached hereto.

The following Examples are illustrative of a preferred mode of carrying out our invention but are not to be construed as limiting the scope thereof. Equivalents thereof will be obvious to one skilled in the art reading this application and said equivalents are contemplated as included within this invention.

EXAMPLE 1

3,2',6'-TRI-N-ACETYLSISOMICIN

A. Via Cupric Acetate Complex

Add cupric acetate hydrate (9 gms., 45 mmol) to a stirred solution of sisomicin (1.3 gms., 2.9 mmol) in water (16 ml.) and dimethylformamide (54 ml.). Stir at room temperature for 35 minutes, then to the cupric salt complex thereby formed add dropwise at a rate of about 25 drops per minute 9.3 ml. of a 1 molar solution of acetic anhydride in dimethylformamide (9.3 mmol). Stir the reaction mixture for an additional 30 minutes, then add 30 ml. of water and bubble hydrogen sulfide through the solution for about 10 minutes, stir the mixture for an additional 30 minutes, then filter the solution through a pad of Celite and wash the cupric sulfide residue with three 20 ml. portions of water. Concentrate the combined filtrate and water washings and chromatograph the resultant residue on silica gel (150 gms., 60–200 mesh) eluting with chloroform:methanol:ammonium hydroxide (30:10:1). Combine like fractions as determined by thin layer chromatography on silica gel using a solvent system consisting of chloroform:methanol:ammonium hydroxide (2:1:0.34) and evaporate the fractions containing the major product in vacuo and lyophilize the resultant aqueous mixture to a residue comprising 3,2',6'-tri-N-acetylsisomicin (1.29 gms., 76% yield); $[\alpha]_D^{26} + 186.7°$ (c, 4.4 in water); pmr (ppm) (D$_2$O); $\delta$1.22 (4''-C-CH$_3$); 1.94, 1.98, 2.0 (N-Acetyls); 2.51 (3''-N-CH$_3$); 2.59 (H-3'', J$_{2'',3''}$=9.5 Hz); 5.10 (H-1'', J$_{1'',2''}$=4.0 Hz); 5.51 (H-1', J$_{1',2'}$=2.5 Hz); mass spectrum (M$^{+\circ}$) m/e 573, also m/e 392, 374, 364, 346, 233, 215, 205, 187; 160; 443, 425, 415, 397; 169. Analysis calculated for C$_{25}$H$_{43}$O$_{10}$N$_5$·H$_2$CO$_3$: C, 49.13; H, 7.14; N, 11.02%. Found: C, 49.10; H, 7.02; N, 11.38%.

B. Via Mixture of Cupric Acetate and Nickel (II) Acetate Complexes (1) Add cupric acetate hydrate (8 gm., 40 mmol) and nickel (II) acetate tetrahydrate (10 gm., 40 mmol) to a stirred solution of sisomicin (8.94 gm. 20 mmol) in dimethylsulfoxide (400 ml.). After 30 minutes at room temperature add dropwise a solution of acetic anhydride (5.4 ml. in 50 ml. tetrahydrofuran, 60 mmol). After the addition is complete, stir the reaction mixture for an additional 30 minutes. Pour the reaction mixture into 1.5 l. of ether and thoroughly mix the contents. After letting the mixture settle, decant the ether layer. Repeat the above procedure three times using 500 ml. ether each time. Dissolve the semi-solid residue in 400 ml. methanol and bubble hydrogen sulfide through the solution to remove cupric and nickel (II) ions. Remove the solids by filtration through Celite and wash the residue with methanol. Concentrate the combined filtrates in vacuo and dissolve the residue in water (150 ml.). Treat the aqueous solution with Amberlite IRA-401S ion exchange resin in the hydroxide cycle until the pH is about 9. Remove the resin by filtration, wash thoroughly and either lyophilize the aqueous solution to give 3,2',6',6'-tri-N-acetylsisomicin in 90% yield (10.3 gms.) or concentrate the aqueous solution to a thick ammonium hydroxide (600 ml.) containing sodium chloride (60 gms.), dry over sodium sulfate and evaporate in vacuo. Chromatograph the resultant residue on silica gel (300-350 gms.) eluting with a chloroform:methanol:concentrated ammonium hydroxide solvent mixture (7:2:0.1 by volume). Combine the like eluates containing the desired product as determined by thin layer chromatography and evaporate the combined eluates in vacuo, then dry the resultant residue at 60° C. and 0.1 mm. to give 3,2',6'-tri-N-(2,2,2-trichloroethoxycarbonyl)sisomicin, yield 7.52 gms. (77% theory); m.p. 124°-127° C. $[\alpha]_D^{26}+91.0°$ (c, 0.5 in chloroform); pmr (ppm) (CDCl$_3$): δ 1.17 (4"-C-$\underline{CH_3}$), 2.58 (3"-N-$\underline{CH_3}$) and 4.77 (-$\underline{CH_2}$CCl$_3$).

B. 3,2',6'-Tri-N-(2,2,2-Trichloroethoxycarbonyl)gentamicin C$_{1a}$

Add cupric acetate hydrate (2.8 gms., 14 mmol) to a stirred solution of gentamicin C$_{1a}$ (1.0 gm., 2.22 mmol) in dimethylsulfoxide (56 ml.) at 25° C. Continue stirring for 1 hour, then to the cupric salt complex thereby formed add portionwise N-(2,2,2-trichloroethoxycarbonyloxy)succinimide (1.8 gms. 62 mmol) over a 15 minute period. Continue stirring for 2 hours, then dilute the reaction mixture with 2 N ammonium hydroxide (800 ml.) and extract with ethyl acetate (3×75 ml.). Evaporate the combined extracts in vacuo and chromatography the resultant residue on a silica gel column (110×2.5 cm.) eluting first with chloroform (250 ml.) and then eluting with chloroform:methanol:concentrated ammonium hydroxide (7:2:0.1 by volume). Combine the like eluates containing the desired product as determined by thin layer chromatography and evaporate the combined eluates to a residue of 3,2',6'-tri-N-(2,2,2-trichloroethoxycarbonyl)gentamicin C$_{1a}$, yield 1.51 gms. (78% theory); $[\alpha]_D^{26}+80.0°$ (c, 0.3 in chloroform), $\nu_{max}^{KBr}$ 3330, 1730, 1520, 1040, 1025 cm$^{-1}$; pmr (ppm) (CDCl$_3$): δ1.14 (4"-C-$\underline{CH_3}$), 2.55 (3"-N-$\underline{CH_3}$) and 4.64 (-$\underline{CH_2}$CCl$_3$).

EXAMPLE 5

3,6'-DI-N-ACETYLAMINOGLYCOSIDES

A. 3,6'-Di-N-Acetylaminoglycosides (1) In a manner similar to that described in Example 1A treat each of the following aminoglycosides with cupric acetate hydrate in aqueous dimethylformamide followed by treatment of the cupric salt complex thereby formed with acetic anhydride in dimethylformamide and thence reaction with hydrogen sulfide.
(1) kanamycin A,
(2) gentamicin B,
(3) gentamicin B$_1$,
(4) gentamicin B$_2$,
(5) gentamicin A$_3$,
(6) 6'-N-methylkanamycin A.

Isolate and purify each of the resultant products in a manner similar to that described in Example 1A to obtain the 3,6'-di-N-acetyl derivatives of each of the foregoing aminoglycosides.

(2) Alternatively, treat each of the aminoglycoside starting compounds of above Example 5A(1) in a manner similar to that described in Example 1B with cupric acetate hydrate, nickel (II) acetate tetrahydrate or cobalt (II) acetate tetrahydrate in dimethylsulfoxide followed by treatment of the salt complex thereby formed with acetic anhydride in tetrahydrofuran and thence reaction with hydrogen sulfide to obtain, upon isolation and purification in the described manner, the corresponding 3,6'-di-N-acetyl derivatives of the starting aminoglycosides.

EXAMPLE 6

3,2'-DI-N-ACETYLAMINOGLYCOSIDES

A. 3,2'-Di-N-Acetylaminoglycosides

Treat each of the following aminoglycosides in a manner similar to that described in Example 5A (1 and 2).
(1) kanamycin C,
(2) Antibiotic G-418,
(3) gentamicin A,
(4) gentamicin A$_1$,
(5) gentamicin X$_1$,
(6) gentamicin X$_2$.

Isolate and purify each of the resultant products in the described manner to obtain the corresponding 3,2'-di-N-acetyl derivatives of each of the starting aminoglycosides.

EXAMPLE 7

2',6'-DI-N-SUBSTITUTED SISOMICIN

A. 2',6'-di-N-(2,2,2-Trichloroethoxycarbonyl)sisomicin Via Nickel (II) Acetate Complex Add sisomicin (5 gms., 11.1 mmol) and nickel (II) acetate hydrate (15 gms., 75 mmol) to methanol (350 ml.) and stir until dissolved. To the solution of the nickel II salt complex thereby formed cooled in an ice bath add N-(2,2,2-trichloroethoxycarbonyloxy)succinimide (6.40 gms., 22 mmol) in portions over a 2 to 3 minute period and stir the reaction mixture at room temperature for an hour. Add concentrated ammonium hydroxide (5 ml.) to the reaction mixture, evaporate in vacuo to a volume of about 100 ml., add 2 N ammonium hydroxide (500 ml.) together with sodium chloride (50 gms.) and extract with chloroform (three 300 ml. portions). Combine the organic phases, dry over sodium sulfate and evaporate. Chromatograph the resultant residue on 300 gms. of silica gel eluting with a chloroform:methanol:concentrated ammonium hydroxide solvent mixture (3:1:0.1 by volume). Combine like fractions containing the desired product as determined by thin layer chromatography and evaporate the combined fractions in vacuo. Dry the precipitate at 60° C. at 0.1 mm. pressure to a residue of 2',6'-di-N-(2,2,2-trichloroethoxycarbonyl)sisomicin, yield=5.80 gms. (72% theory); m.p. 115°-119° C.; $[\alpha]_D^{26}+94°$ C. (c, 0.4 in chloroform); pmr (ppm) (CDCl$_3$): δ 1.16 (4"-C-$\underline{CH_3}$); 1.33 (H-2, J$_{2ax,2eq}$=J$_{1,2ax}$=J$_{2ax,3}$=10 Hz); 2.60 (3"-N-$\underline{CH_3}$); 4.73 (-$\underline{CH_2}$CCl$_3$); 4.95 (H-1" and H-4'); 5.50 (H-1', J$_{1',2'}$=3 Hz); 6.28 (2'-$\underline{NH}$, J=8 Hz) and 7.45 (6'-$\underline{NH}$).

B. 2',6'-Di-N-Tert.-Butoxycarbonylsisomicin Via Cupric Acetate Complex

Add cupric acetate hydrate (0.6 gm., 3 mmol) to a solution of sisomicin (447 mg., 1 mmol) in dimethylsulfoxide (10 ml.), and stir for 10 minutes at room temperature. To the cupric salt complex thereby formed add dropwise a solution of N-tert.-butoxycarbonyloxyphthalimide (576 mg., 2.2 mmol) in dimethylsulfoxide (3 ml.). Stir for 18 hours at room temperature, then add the reaction solution dropwise into stirred diethyl ether (75 ml.). Allow the resultant precipitate to settle, decant the diethyl ether solution and triturate the precipitate twice syrup, dissolve the residue in minimum amount of isopropanol and precipitate the product with excess ether.

(2) Alternatively, after removal of the cupric and nickel (II) ions by treatment with hydrogen sulfide and filtration, concentrate the filtrate and dissolve the residue in a minimum amount of isopropanol and precipitate the product with excess ether to obtain 3,2',6'-tri-N-acetylsisomicin acetic acid salt in 90% yield.

C. Via Cobalt (II) Acetate Complex (1) Stir sisomicin (0.447 gms., 1 mmol) in dimethylformamide (20 ml.) and add cobalt (II) acetate tetrahydrate (0.516 gms., 2.07 mmol). Stir for 20 minutes at room temperature, then to the cobalt (II) acetate complex thereby formed add dropwise a 1 molar solution of acetic anhydride in tetrahydrofuran (3 ml.). Continue stirring for 1 hour, then add water (10 ml.) and bubble hydrogen sulfide through the solution until all the cobalt (II) is precipitated. Remove the cobalt (II) sulfide by filtration through a pad of Celite and wash the residue with water. Evaporate the filtrate in vacuo and dissolve the resultant residue in a minimum quantity of chloroform:methanol:ammonium hydroxide (2:1:0.35). Pass the solution through a column of silica gel (50 gms., 60–200 mesh), washing the column with the same solvent. Collect the homogeneous fractions containing the 3,2',6'-tri-N-acetylsisomicin as determined by thin layer chromatography, evaporate the combined fractions in vacuo and lyophilize the resultant residue to obtain 3,2',6'-tri-N-acetylsisomicin (yield=0.498 gms., 88% theory).

(2) In the above procedure, by substituting dimethylsulfoxide for dimethylformamide and by isolating and purifying the resultant product in a manner similar to that described in Example 1B, there is obtained 3,2',6'-tri-N-acetylsisomicin in good yields.

D. Utilizing Acetyl-Acetone as Transition Metal Precipitating Reagent

In the procedures of Examples 1A, 1B and 1C in place of hydrogen sulfide utilize acetyl-acetone as the transition metal precipitating reagent and separate by filtration the resultant precipitate of the corresponding transition metal acetyl-acetonate, then isolate and purify each of the resultant products in a manner similar to that described to obtain 3,2',6'-tri-N-acetylsisomicin.

EXAMPLE 2

3,2',6'-TRI-N-ACETYLVERDAMICIN VIA CUPRIC ACETATE COMPLEX

To a stirred solution of verdamicin (4.61 gms., 10 mmol) in dimethylformamide (300 ml.) and water (90 ml.) add cupric acetate monohydrate (14 gms., 70 mmol), stir the reaction mixture at room temperature for about 30 minutes, then to the cupric salt complex thereby formed add dropwise 33 ml. of a 1 molar solution of acetic anhydride in dimethylformamide (3.3 equivalents). Continue stirring at room temperature for about 18–20 hours, then add water and bubble hydrogen sulfide gas through the solution. Filter off the copper sulfide thereby formed through filter aid on a sintered glass funnel rinsing with water (50–200 ml.). Evaporate the filtrate in vacuo, dissolve the resultant residue in water and adjust the pH of the aqueous solution to about 9 using Amberlite IRA-401S ion exchange resin in the hydroxide form. Freeze dry the solution to a residue comprising 3,2',6'-tri-N-acetylverdamicin (5.5 gms.). Purify by chromatographing on 300 gm. silica gel (60–200 mesh) eluting with chloroform:methanol:ammonium hydroxide (28%) (30:10:1). Combine like fractions as determined by thin layer chromatography and evaporate the combined fractions in vacuo to a residue comprising 3,2',6'-tri-N-acetylverdamicin, yield 1.68 gm. (2.8 mmol, 28% theory); pmr (ppm) (D$_2$O): $\delta$1.25 (4"-C-$\underline{CH_3}$); 1.36 (6'-C-$\underline{CH_3}$, J$_{6',7'}$=7 Hz); 1.97, 2.04 (N-Acetyls); 2.56 (3"-N-$\underline{CH_3}$); 4.91 (H-4"); 5.11 (H-1', J$_{1',2'}$=4 Hz); 5.60 (d, H-1''', J$_{1'',2''}$=2.5 Hz); mass spectrum: m/e 587 [M]$\cdot$+; 392, 374, 364, 346; 233, 215, 205, 187; 457, 439, 429, 411; 183.

EXAMPLE 3

3,2',6'-TRI-N-ACETYLAMINOGLYCOSIDES VIA CUPRIC ACETATE AND NICKEL (II) ACETATE COMPLEXES

A. 3,2',6'-Tri-N-Acetylaminoglycosides

In a manner similar to that described in Example 1B treat each of the following aminoglycosides with cupric acetate hydrate and nickel (II) acetate tetrahydrate in dimethylsulfoxide followed by treatment of the salt complex thereby formed with acetic anhydride in tetrahydrofuran, and thence treatment with hydrogen sulfide.

(1) gentamicin C$_1$,
(2) gentamicin C$_{1a}$,
(3) gentamicin C$_2$,
(4) gentamicin C$_{2a}$,
(5) gentamicin C$_{2b}$,
(6) verdamicin,
(7) tobramycin,
(8) Antibiotic 66-40B,
(9) Antibiotic 66-40D,
(10) Antibiotic JI-20A,
(11) Antibiotic JI-20B,
(12) Antibiotic G-52,
(13) 5-epi-, 5-deoxy-, and 5-epi-azido-5-deoxy analogs of the foregoing,
(14) kanamycin B,
(15) 3',4'-dideoxykanamycin B,
(16) nebramycin factor 4,
(17) nebramycin factor 5',
(18) 3',4'-dideoxy-3',4'-dehydrokanamycin B, and
(19) 3',4'-dideoxy-6'-N-methylkanamycin B.

Isolate and purify each of the resultant products in a manner similar to that described in Examples 1 and 2 to obtain the 3,2',6'-tri-N-acetyl derivatives of each of the foregoing aminoglycosides.

EXAMPLE 4

3,2',6'-TRI-N-(2,2,2-TRICHLOROETHOXYCARBONYL) DERIVATIVES OF SISOMICIN AND GENTAMICIN C$_{1a}$ VIA CUPRIC ACETATE COMPLEX

A.

3,2',6'-Tri-N-(2,2,2-Trichloroethoxycarbonyl)sisomicin

Add cupric acetate hydrate (14 gms., 70 mmol) to a stirred solution of sisomicin (5.0 gms., 11.1 mmol) in dimethylsulfoxide (300 ml.) stirring for 45 minutes, then to the cupric salt complex thereby formed add in portions N-(2,2,2-trichloroethoxycarbonyloxy)succinimide (9.25 gms., 32 mmol) (over a 2 to 3 minute period). Stir the resulting green solution for one hour, then dilute the reaction mixture with 2 N ammonium hydroxide (3 liters) and extract with ethyl acetate (two 600 ml. portions). Combine the organic extracts, wash with 2 N with 75 ml. portions of diethyl ether. Dissolve the precipitate in methanol, and bubble hydrogen sulfide through the methanol solution, separate the resultant cupric sulfide precipitate by filtration, deionize the methanolic solution with Amberlite IRA-401S (OH$^\ominus$) ion exchange resin (20 gm.), filter, concentrate the filtrate in vacuo and chromatograph the resultant residue on alumina (75 gms.) in a column (2.4×30 cm.) eluting with chloroform:methanol:concentrated ammonium hydroxide (30:10:1 by volume). Combine the like fractions containing the desired product as determined by thin layer chromatography and evaporate the combined fractions and freeze dry the resultant residue to give 2′,6′-di-N-tert.-butoxycarbonylsisomicin, yield 258 mg. (40% theory); mass spectrum: (M+.) m/e 647, also m/e 547; 530; 517, 499, 489, 471; 462; 350, 332, 322, 304; 191; 160.

C. 2′,6′-Di-N-Tert.-Butoxycarbonylsisomicin Via Cobalt (II) Acetate Complex or Via Nickel (II) Acetate Complex In the procedure of Example 7B, by utilizing methanol as solvent (instead of dimethylsulfoxide) and either nickel (II) acetate or cobalt (II) acetate as transition metal salt (instead of cupric acetate) there is obtained 2′,6′-di-N-tert.-butoxycarbonylsisomicin in improved yields.

EXAMPLE 8

1,3,2′,6′-TETRA-N-ACETYLSISOMICIN VIA CUPRIC ACETATE COMPLEX

Add cupric acetate hydrate (49 gms., 24.5 mmol) to a stirred solution of sisomicin (22 gms., 49.2 mmol) in 91% aqueous methanol. Continue stirring the solution in an ice water bath for 15 minutes, then to the cupric salt complex thereby formed add dropwise over a period of 10 minutes 21 ml. of acetic anhydride (226 mmol) keeping the temperature below 25° C. Stir the reaction mixture for 3 hours at room temperature, then bubble hydrogen sulfide through the solution. Remove the resultant precipitate of cupric sulfide by filtration through Celite and wash the residue with methanol. Combine the filtrate and washings and concentrate in vacuo. Chromatograph the resultant residue on 600 gms. silica gel (60–200 mesh) eluting with a solvent mixture of chloroform:methanol:concentrated ammonium hydroxide (30:10:1). Combine like fractions containing the desired product as determined by thin layer chromatography and evaporate in vacuo and lyophilize the resultant residue to give 1,3,2′,6′-tetra-N-acetylsisomicin, yield 23.5 gms. (78% theory); $[\alpha]_D^{26}+191°$ (c, 0.2 in water); pmr (ppm) (D$_2$O): $\delta$ 1.18 (C-$\underline{CH}_3$); 1.88–1.98 (N-$\underline{CH}_3$); 2.48 (N-acetyls); 4.88 (H-4′); 5.07 (H-1″, $J_1″,_2″=4$ Hz); 5.48 (H-1′, $J_1′,_2′=3$ Hz); mass spectrum: (M+.) m/e 615; also m/e 592, 550; 485, 467, 457, 439; 434, 416, 406, 388; 275, 257, 247, 229; 211; 160.

EXAMPLE 9

1,3,2′-TRI-N-ACETYLSISOMICIN

A. 6′-N-Trifluoroacetylsisomicin Via Cupric Acetate Complex

Add cupric acetate hydrate (17.48 gms., 87.3 mmol) to a stirred solution of sisomicin (40 gms., 89.5 mmol) in 95% aqueous methanol (3.12 liters). Stir for 5 minutes, then to the cupric salt complex thereby formed add dropwise over a period of 3 minutes ethyl trifluorothiol acetate (11.65 ml., 91.9 mmol). Continue stirring for 1 hour, then add an additional portion of ethyl trifluorothiol acetate (1.6 ml., 12.45 mmol). This reaction solution containing 6′-N-trifluoroacetylsisomicin is used as is in the procedure of Example 9B.

B. 1,3,2′-Tri-N-Acetylsisomicin

Cool the reaction mixture prepared in Example 9A in an ice water bath and add dropwise acetic anhydride (28 gms., 280 mmol) at a rate of 25 drops per minute. Stir for 18 hours at room temperature, then bubble hydrogen sulfide through the solution for 10 minutes. Remove the precipitated cupric sulfide by filtration through a pad of Celite. Evaporate the filtrate in vacuo, dissolve the resultant residue in concentrated ammonium hydroxide (1 liter) and stir for 3 hours at room temperature. Concentrate the solution in vacuo and chromatograph the resultant residue on 4.5 kilograms of silica gel (60–200 mesh) eluting with a solvent system consisting of chloroform:methanol:concentrated ammonium hydroxide (30:10:1). Combine the like fractions containing the desired product as determined by thin layer chromatography, concentrate the combined fractions in vacuo and lyophilize the resultant residue to give 1,3,2′-tri-N-acetylsisomicin; $[\alpha]_D^{26}+191.5°$ (c, 0.3 in water), pmr (ppm) (D$_2$O): $\delta$ 1.31 (C-$\underline{CH}_3$); 1.92, 1.94, 1.96 (N-acetyls); 2.82 (N-$\underline{CH}_3$); 5.15 (H-1″, $J_1″,_2″=3.5$ Hz); 5.55 (H-1′,$J_1′,_2′=2.5$ Hz); mass spectrum: (M+.) 573 also m/e 443, 425, 415, 397; 275, 257, 247, 229; 434, 416, 406, 388; 169, 160.

EXAMPLE 10

6′-N-HYDROCARBONYLOXYCARBONYLAMINOGLYCOSIDES

A. 6′-N-Benzyloxycarbonylgentamicin B Via Cupric Chloride Complex

Add cupric chloride dihydrate (0.34 gms., 2 mmol) to a stirred solution of gentamicin B (0.964 gms., 2 mmol) in water (3 ml.) and dimethylsulfoxide (30 ml.). Stir at room temperature for 20 minutes, then add dropwise to the cupric salt complex thereby formed in situ a solution of N-benzyloxycarbonyloxyphthalimide (1.105 gms., 4 mmol) in dimethylsulfoxide (5 ml.). Monitor the progress of the reaction via thin layer chromatography on silica gel using a solvent system consisting of chloroform:methanol:concentrated ammonium hydroxide (2:1:0.35). When the reaction is complete as evidenced by thin layer chromatography (about 3 hours) add water (10 ml.) to the reaction mixture and bubble hydrogen sulfide through the solution. Remove the resultant precipitate of cupric sulfide by filtration through a pad of Celite and wash the residue with methanol. Stir the combined filtrate methanol wash with Amberlite IRA-401S (OH$^\ominus$) ion exchange resin. Filter off the resin and wash with methanol. Evaporate the combined filtrate and methanol wash in vacuo using benzene as a co-solvent until all the water is removed. Pour the resulting concentrated reaction solution into a large volume of methylene chloride with stirring. Separate the resulting precipitate by filtration and wash the precipitate with ether to obtain 6′-N-benzyloxycarbonylgentamicin B; yield 100%; pmr (ppm) (D$_2$O): $\delta$ 1.26 (4″-C-$\underline{CH}_3$): 2.65 (3″-N-$\underline{CH}_3$); 5.13 and 7.43 (O-$\underline{CH}_2$-$\underline{C_6H_5}$).

B. In the procedure of above Example 10A substitute for gentamicin B any aminoglycoside antibacterial agent having a primary carbinamine at C-5′ to obtain the corresponding 6′-N-benzyloxycarbonylaminoglycoside, e.g. sisomicin, gentamicin C$_{1a}$, gentamicin A, Antibiotic JI-20A, Antibiotic 66-40B, Antibiotic 66-40D, the 5-epi-, 5-epi-azido-5-deoxy- and 5-epi-amino-5-deoxy analogs of the foregoing, Antibiotic Mu-1, Antibiotic Mu-2, Antibiotic Mu-4, Antibiotic Mu-5, tobramycin, kanamycin A, kanamycin B, Antibiotic BBK-8, Antibiotic XK-88-3 and Antibiotic XK-88-5.

C. In the procedure of Examples 10A and 10B by substituting for N-benzyloxycarbonyloxyphthalimide equivalent quantities of other phthalimide reagents, e.g. N-tert.-butoxycarbonyloxyphthalimide or N-(2,2,2-trichloroethoxycarbonyloxy)phthalimide, there is obtained the corresponding 6'-N-hydrocarbonyloxycarbonylaminoglycoside, e.g. the corresponding 6'-N-tert.-butoxycarbonylaminoglycoside and 6'-N-(2,2,2-trichloroethoxycarbonyl)aminoglycoside derivatives.

D. 6'-N-Tert.-Butoxycarbonylgentamicin B Via Cupric Acetate Complex

Add cupric acetate hydrate (24 gms. 120 mmol) to a stirred solution of gentamicin B (19.28 gms., 40 mmol) in dimethylsulfoxide (1 liter). Continue stirring for 20 minutes, to the cupric salt complex thereby formed in situ add a solution of N-tert.-butoxycarbonyloxyphthalimide (16 gms., 61 mmol) in dimethylsulfoxide (200 ml.) over a period of 20 minutes. Stir for 18 hours at room temperature, then bubble hydrogen sulfide through the solution to precipitate cupric sulfide. Remove the solids by filtration through a pad of Celite and wash the residue with 200 ml. of water. Stir the combined filtrate and washings with 200 ml. of Amberlite IRA-401S (OH$^\ominus$) ion exchange resin for one hour. Remove the resin by filtration, wash with water, and concentrate the combined filtrate and washings in vacuo using benzene to azeotrope with water. Dissolve the resultant residue in methanol and pour the methanol solution into excess ether with stirring. Filter and air dry the resultant precipitate comprising 6'-N-tert.-butoxycarbonylgentamicin B, yield 23 gm. (100% theory); $[\alpha]_D^{26}+124°$ (c, 1 in methanol). pmr (ppm) (D$_2$O): δ 1.21 (4"-C-CH$_3$); 1.42 (t-butyl); 2.55 (3"-N-CH$_3$); 5.06 (H-1", J$_1$",$_2$"=4.0 Hz); 5.21 (H-1', J$_1$',$_2$'=3.0 Hz). Analysis Calculated for C$_{24}$H$_{46}$N$_4$O$_{12}$.CO$_2$.H$_2$O: C, 46.57; H, 7.51; N, 8.68%. Found: C, 46.80; H, 7.82; N, 8.54%.

EXAMPLE 11

3,6'-DI-N-HYDROCARBONYLOXYCARBONYL AMINOGLYCOSIDES

A. 3,6'-Di-N-Benzyloxycarbonylgentamicin B via Mixture of Cupric Acetate and Nickel (II) Acetate Complexes Add cupric acetate hydrate (8 gms., 40 mmol) and nickel (II) acetate tetrahydrate (9.92 gms., 40 mmol) to a stirred solution of gentamicin B (9.64 gms., 20 mmol) in dimethylsulfoxide (400 ml.). Stir at room temperature for 30 minutes, then to the cupric-nickel (II) salt complex thereby formed add N-benzyloxycarbonyloxyphthalimide (14 gms., 47.2 mmol) in dimethylsulfoxide (70 ml.) dropwise over a 10 minute period. Stir for one hour at room temperature, then pour the reaction mixture into ether (4 l.) and shake for one minute. Allow the oil to settle and decant off the supernatant ether. Repeat this procedure two more times using 1500 ml. and 1000 ml., respectively, of diethyl ether. Dissolve the resultant gummy residue thereby obtained in methanol (400 ml.) and concentrated ammonium hydroxide (40 ml.) and bubble hydrogen sulfide through the solution, separate the resultant precipitate comprising cupric sulfide and nickel sulfide by filtration through a pad of Celite. Wash the residue with methanol, then stir the combined filtrate and methanol wash with Amberlite IRA-401S (OH$^\ominus$) ion exchange resin (400 ml.) to remove the N-hydroxy phthalimide. Filter the solution, wash the resin with methanol, then evaporate the combined filtrate and methanol wash in vacuo, and chromatograph the resultant residue on silica gel (900 gms.) eluting with chloroform:methanol:concentrated ammonium hydroxide (30:10:1). Combine the like fractions containing the desired product as determined by thin layer chromatography and evaporate the combined fractions in vacuo to a residue comprising the 3,6'-di-N-benzyloxycarbonylgentamicin B; yield 10.86 gms. (75% theory); $[\alpha]_D^{26}+105.3°$ (c, 4.07 in water). Analysis Calculated for: C$_{35}$H$_{50}$O$_{14}$N$_4$.CO$_2$.2H$_2$O: C, 52.04; H, 6.55; N, 6.74%. Found: C, 51.94; H, 6.33; N, 6.83%.

B. 3,6'-di-N-Benzyloxycarbonylgentamicin B Via Cobalt (II) Acetate Complex

Dissolve gentamicin B (4.82 gms., 10 mmol) in dimethylsulfoxide (195 ml.) and water (5 ml.). Add triethylamine (2 ml.) and stir. Add cobalt (II) acetate tetrahydrate (7.08 gms., 28.5 mmol), continue stirring for 30 minutes, then to the gentamicin B-cobalt (II) acetate complex thereby formed add in a dropwise manner a solution of N-(benzyloxycarbonyloxy)phthalimide (6.5 gms., 20 mmol) in dimethylsulfoxide (20 ml.) and stir for 3 hours, then pour into ether and isolate in the manner described in Example 11A. Purify the resultant residue by dissolving in a small amount of methanol and adding ethyl acetate followed by excess diethyl ether. Separate the resultant precipitate by filtration and air dry to obtain pure 3,6'-di-N-benzyloxycarbonylgentamicin B, yield 90% theory.

C. 3,6'-di-N-Benzyloxycarbonylgentamicin B Via Cadmium (II) Acetate Complex Dissolve gentamicin B (4.82 gms., 10 mmol) in dimethylsulfoxide (195 ml.) and add cadmium (II) acetate dihydrate (7.98 gms., 30 mmol). Stir for 30 minutes, then to the gentamicin B cadmium (II) acetate complex thereby formed add a solution of N-(benzyloxycarbonyloxy)phthalimide (6.5 gms., 20 mmol) in dimethylsulfoxide (20 ml.). Stir for 3 hours at room temperature, then isolate and purify in a manner similar to that described in Example 11A to obtain 3,6'-di-N-benzyloxycarbonylgentamicin B.

D. 3,6'-Di-N-Benzyloxycarbonylkanamycin A Via Nickel (II) Acetate Complex

Add nickel (II) acetate tetrahydrate (24.8 gms., 10 mmol) to a stirred solution of kanamycin A (9.7 gms., 20 mmol) in dimethylsulfoxide (400 ml.). Stir at room temperature for 30 minutes, then to the resulting nickel (II) salt complex thereby formed add N-benzyloxycarbonyloxyphthalimide (13.0–15.6 gms., 44–52.6 mmol) in dimethylsulfoxide (70 ml.) over a 10 minute period. Stir at room temperature for one hour, then pour the reaction mixture into ether (2500 ml.) and shake one minute. Allow the oil to settle and decant the supernatant dimethylsulfoxide ether. Repeat this procedure two more times using 1500 ml. and 1000 ml., respectively, of ether. Dissolve the resultant gummy residue in methanol (1000 ml.) and concentrated ammonium hydroxide (50 ml.). Bubble hydrogen sulfide through the solution and separate the resultant precipitate of nickel (II) sulfide through a pad of Celite and wash the residue with methanol. Stir the combined filtrate and methanol wash with Amberlite IRA-401S (OH⊖) ion exchange resin (300 gms.), filter off the resin and evaporate the filtrate in vacuo. Triturate the resultant gummy residue with a 50:50 mixture of acetonitrile:ether and filter the resultant white solid to obtain 3,6'-di-N-benzyloxycarbonylkanamycin A; yield 12.5 gms. (83.5% theory); $[\alpha]_D^{26}+78°$ (c, 4.84 in 50% aqueous methanol). Analysis Calculated for: $C_{34}H_{48}O_{15}N_4.H_2O$; C, 56.2; H, 6.75; N, 6.94%. Found: C, 51.02; H, 6.26; N, 6.85%.

E. Treat each of the following aminoglycosides with a mixture of cupric acetate hydrate and nickel (II) acetate tetrahydrate or with cobalt (II) acetate tetrahydrate or with cadmium (II) acetate dihydrate according to the procedures of Examples 11A through 11D, respectively.
(1) gentamicin $B_1$,
(2) gentamicin $A_3$,
(3) 6'-N-methylkanamycin A.

Isolate and purify each of the resulting products to obtain, respectively,
(1) 3,6'-di-N-benzyloxycarbonylgentamicin $B_1$,
(2) 3,6'-di-N-benzyloxycarbonylgentamicin $A_3$,
(3) 3,6'-di-N-benzyloxycarbonyl-6'-N-methylkanamycin A.

F. Preparation of 3,6'-Di-N-Tert.-Butoxycarbonylgentamicin B from 6'-Tert.-Butoxycarbonylgentamicin B Via Cupric Acetate Complex To a solution of 6'-N-tert.-butoxycarbonylgentamicin B (10 gms., 17.1 mmol) in dimethylsulfoxide (300 ml.), add cupric acetate monohydrate (6.9 gms., 34.5 mmol) and stir for 20 minutes. To the cupric salt complex thereby formed in situ add dropwise a solution of N-tert.-butoxycarbonyloxyphthalimide (4.5 gms., 17.1 mmol) in dimethylsulfoxide (20 ml.). Continue stirring for 2 hours, then add an additional 2.4 gms. of N-tert.-butoxycarbonyloxyphthalimide and continue stirring the reaction mixture for 10 hours. Pour the reaction mixture into ether (1.5 liters) with stirring. Allow the resultant precipitate or oil to settle and carefully decant the supernatant liquid. Wash the residue two times with ether (300 ml.). Dissolve the resultant residue in methanol (100 ml.) and bubble hydrogen sulfide through the solution to precipitate cupric sulfide completely. Remove the solids by filtration through a pad of Celite and wash with methanol. Stir the methanolic solution with just enough Amberlite IRA-401S (OH⊖) ion exchange resin to bring the pH to about 9 and remove N-hydroxyphthalimide. Remove the resin by filtration, wash with methanol, and concentrate the combined filtrate and washings to a volume of about 50 ml. containing 3,6'-di-N-tert.-butoxycarbonylgentamicin B, which may be used without further purification as starting compound in the procedure of Examples 18A and 21B. To isolate the compound, crystallize by triturating the residue after evaporation with ether to give 3,6'-di-N-tert.-butoxycarbonylgenatamicin B (yield = 90% theory). Alternatively, purify by chromatographing on silica gel (ratio of compound: silica gel = 1:40) using chloroform:methanol:ammonium hydroxide (2:1:0.35) as the developing solvent mixture. Pool the like fractions containing 3,6'-di-N-tert.-butoxycarbonylgentamicin B as determined by thin layer chromatography, concentrate and lyophilize to give 3,6'-di-N-tert.-butoxycarbonylgentamicin B; $[\alpha]_D^{26}+113.3°$ (c, 0.39 in water); pmr (ppm) (D$_2$O): δ1.17 (4''-C-$\underline{CH}_3$); 1.38 (t-butyl); 2.5 (3''-N-$\underline{CH}_3$); 2.54 (H-3'', $J_{2'',3''}=10$ Hz); 4.02 (H-5'' eq, $J_{5''\text{ax,eq}}=12$ Hz); 5.04 (H-1'', $J_{1'',2''}=3.5$ Hz); 5.23 (H-1', $J_{1',2'}=3.0$ Hz).

Analysis calculated for $C_{29}H_{57}O_{15}N_4.H_2O$: C, 49.63; H, 8.19; N, 7.98%. Found: C, 49.83; H, 7.81; N, 7.68%.

G. 3,6'-Di-N-Tert.-Butoxycarbonylgentamicin B from Gentamicin B Via Cupric Acetate Complex Add cupric acetate monohydrate (5.0 gms., 25 mmol) to a stirred solution of gentamicin B (4.82 gms., 10 mmol) in dimethylsulfoxide (250 ml.). Stir for 30 minutes, then to the cupric salt complex thereby formed in situ add dropwise a solution of N-tert.-butoxycarbonyloxyphthalimide (10.5 gms., 40 mmol) in dimethylsulfoxide (20 ml.). Stir at room temperature for 2 hours, then add additional N-tert.-butoxycarbonyloxyphthalimide (1.5 gms., 5.7 mmol). Stir for 16 hours, then again add an additional N-tert.-butoxycarbonyloxyphthalimide (0.35 gms., 1.33 mmol). Continue stirring for 6 hours, then pour the reaction mixture into 1.5 l of stirred ether. Stir for 30 minutes, allow the reaction mixture to stand, decant the supernatant solution, again add 500 ml. of ether to the residue, let stand and decant the supernatant solution. Dissolve the resultant residue in 100 ml. of mehanol and bubble hydrogen sulfide for 15 minutes. Remove the cupric sulfide solid by filtration through a pad of Celite and wash the residue with methanol. Treat the methanolic solution with Amberlite IRA-401S (OH⊖) ion exchange resin to bring the pH of the solution to about 8.5–9.0, remove the solids by filtration and wash the solids with methanol. Evaporate the solution to near dryness and lyophilize from water. Crystallize 3,6'-di-N-tert.-butoxycarbonylgentamicin B by triturating with ether. Alternatively, the crude concentrate may be used as starting material in the procedure of Examples 18A and 21B.

EXAMPLE 12

OTHER 3,2',6'-TRI-N-ACYLAMINOGLYCOSIDES

A. 3,2',6'-Tri-N-Benzyloxycarbonylgentamicin $C_2$ Via Mixture of Cupric Acetate Complex and Nickel (II) Acetate Complex Add cupric acetate hydrate (0.6 gms., 3 mmol) and nickel (II) acetate tetrahydrate (0.743 gms., 3 mmol) to a stirred solution of gentamicin $C_2$ (0.925 gms., 2 mmol) in dimethylsulfoxide (40 ml.). Stir at room temperature for 30 minutes, then to the mixed cupric and nickel salt complex thereby formed add N-benzyloxycarbonyloxyphthalimide (1.8 gms., 6.5 mmol) in dimethylsulfoxide (7 ml.) over a 10 minute period. Continue stirring for one hour, then pour the reaction mixture into ether (400 ml.) with stirring. Decant the supernatant ether, repeat the foregoing process using 200 ml. and 100 ml. of ether, respectively. Dissolve the resulting gummy residue in methanol (100 ml.) and concentrated ammonium hydroxide (5 ml.), then bubble hydrogen sulfide through the solution. Remove the resultant precipitate of cupric sulfide and nickel (II) sulfide by filtration through a pad of Celite, wash the precipitate with methanol then stir the combined filtrate and methanol wash with Amberlite IRA-401S (OH⊖) ion exchange resin. Separate the resin by filtration and wash with methanol. Evaporate the combined filtrate and methanol wash in vacuo, then chromatograph the resultant gummy residue on silica gel (50 gms.) eluting with chloroform:methanol:concentrated ammonium hydroxide (30:10:1). Combine the like fractions containing the desired product as determined by thin layer chromatography and evaporate the combined eluates to a residue comprising 3,2′,6′-tri-N-benzyloxycarbonylgentamicin $C_2$; yield 1.4 gms. (81% theory): mass spectrum: m/e 484; 411; 325; 160.

B. In a manner similar to that described in Example 12A, treat each of the aminoglycoside starting compounds (1), (2) and (4)–(20) listed in Example 3A with cupric acetate hydrate and nickel (II) acetate tetrahydrate in dimethylsulfoxide followed by treatment of the salt complex thereby formed with N-benzyloxycarbonyloxyphthalimide and thence treatment with hydrogen sulfide and isolation and purification of each of the resultant products to obtain, respectively, (1) 3,2′,6′-tri-N-benzyloxycarbonylgentamicin $C_1$, yield 1.3 gms., 72.5% theory. Mass spectrum: m/e 749; 615; 484, 466, 456; 425, 407; 325, 307, 297; 291; 160.
(2) 3,2′,6′-tri-N-benzyloxycarbonylgentamicin $C_{1a}$,
(4) 3,2′,6′-tri-N-benzyloxycarbonylgentamicin $C_{2a}$,
(5) 3,2′,6′-tri-N-benzyloxycarbonylgentamicin $C_{2b}$,
(6) 3,2′,6′-tri-N-benzyloxycarbonylverdamicin,
(7) 3,2′,6′-tri-N-benzyloxycarbonyltobramycin,
(8) 3,2′,6′-tri-N-benzyloxycarbonyl-Antibiotic 66-40B,
(9) 3,2′,6′-tri-N-benzyloxycarbonyl-Antibiotic 66-40D,
(10) 3,2′,6′-tri-N-benzyloxycarbonyl-Antibiotic JI-20A,
(11) 3,2′,6′-tri-N-benzyloxycarbonyl-Antibiotic JI-20B,
(12) 3,2′,6′-tri-N-benzyloxycarbonyl-Antibiotic G-52,
(13) 5-epi-, 5-deoxy-, and 5-epi-azido-5-deoxy analogs of the foregoing,
(14) 3,2′,6′-tri-N-benzyloxycarbonylkanamycin B,
(15) 3,2′,6′-tri-N-benzyloxycarbonyl-3′,4′-dideoxykanamycin B,
(16) 3,2′,6′-tri-N-benzyloxycarbonylnebramycin factor 4,
(17) 3,2′,6′-tri-N-benzyloxycarbonylnebramycin factor 5′,
(18) 3,2′,6′-tri-N-benzyloxycarbonyl-3′,4′-dideoxy-3′,4′-dehydrokanamycin B, and
(19) 3,2′,6′-tri-N-benzyloxycarbonyl-3′,4′-dideoxy-6′-N-methylkanamycin A.

C. In the procedures of Examples 12A and 12B, substitute for the N-benzyloxycarbonyloxyphthalimide reagent equivalent quantities of N-tert.-butoxycarbonyloxyphthalimide or N-(2,2,2-trichloroethoxycarbonyloxy)succinimide to obtain the corresponding 3,2′,6′-tri-N-tert.-butoxycarbonylaminoglycoside and 3,2′,6′-tri-N-(2,2,2-trichloroethoxycarbonyl)aminoglycoside, respectively.

D. Mixed 3,2′,6′-Tri-N-Acylaminoglycosides and Conversion to 3,6′-Di-N-Acylaminoglycoside (1)
6′-N-Acetyl-2′-N-(2,2,2-Trichloroethoxycarbonyl)-sisomicin Via Cupric Acetate Complex In a manner similar to that described in Example 7A treat 6′-N-acetylsisomicin with about 7 equivalents of cupric acetate hydrate in methanol, then to the cupric salt complex thereby formed add in portions about 1 equivalent of N-(2,2,2-trichloroethoxycarbonyl)succinimide. Stir the reaction mixture for one hour, then treat with ammonium hydroxide, and isolate and purify the resultant product in a manner similar to that described in Example 7A to obtain 2′-N-(2,2,2-trichloroethoxycarbonyl)-6′-N-acetylsisomicin.

(2)
3,6′-Di-N-Acetyl-2′-N-(2,2,2-Trichloroethoxycarbonyl)sisomicin Via Cupric Acetate Complex Add cupric acetate hydrate (24 gms., 120 mmol) to a stirred solution of 2′-N-(2,2,2-trichloroethoxycarbonyl)-6′-N-acetylsisomicin (26.5 gms., 40 mmol) in dimethylsulfoxide (1 liter). Continue stirring for 20 minutes, then to the cupric salt complex thereby formed add dropwise at the rate of about 25 drops per minute 40 ml. of a 1 molar solution of acetic anhydride in tetrahydrofuran (40 mmol). Stir the reaction mixture for an additional 30 minutes, then pour into ether (8 l.). Shake well and set aside. Decant the ether layer and wash the residue twice more with 1 liter ether each time. Dissolve the residue in methanol (800 ml.) and bubble hydrogen sulfide for 15 minutes. Stir the mixture for an additional 30 minutes, then filter the solution through a pad of Celite and wash the cupric sulfide residue with water. Concentrate the combined filtrate and water washings and chromatograph the resultant residue on silica gel eluting with chloroform:methanol:ammonium hydroxide (30:10:1). Combine like fractions containing the desired product as determined by thin layer chromatography and evaporate the combined fractions in vacuo to a residue comprising 3,6′-di-N-acetyl-2′-N-(2,2,2-trichloroethoxycarbonyl)sisomicin.

(3) 3,6′-Di-N-Acetylsisomicin

Add 3.9 molar equivalents of zinc powder to a solution of 3,6′-di-N-acetyl-2′-N-(2,2,2-trichloroethoxycarbonyl)sisomicin in 10% acetic acid in methanol. Heat the solution at reflux temperature for two hours monitoring the reaction by thin layer chromatography on silica gel using chloroform:methanol:ammonium hydroxide (30:10:1) as solvent system. When the reaction is complete as determined by thin layer chromatography, filter the solution, add sodium carbonate to the filtrate, filter and concentrate the filtrate in vacuo. Purify by chromatographing the resultant residue on silica gel eluting with chloroform:methanol:ammonium hydroxide (30:10:1). Combine the like fractions containing the desired product as determined by thin layer chromatography, then evaporate the combined fractions in vacuo and lyophilize the resultant aqueous mixture to a residue comprising 3,6′-di-N-acetylsisomicin.

EXAMPLE 13

1,3,2′,3″-TETRA-N-ACETYLSISOMICIN VIA CUPRIC ACETATE COMPLEX

A. 6′-N-Trifluoroacetylsisomicin Via Cupric Acetate Complex

Dissolve sisomicin (39.1 gms., 87.5 mmol) in methanol (2950 ml.) and water (200 ml.). While stirring add cupric acetate hydrate (8.92 gms., 4.47 mmol). Stir for 15 minutes, then add dropwise over a period of three minutes ethyl trifluorothiolacetate (11.55 ml., 14.2 gms., 90 mmol) followed by an additional 1.3 ml. (1.6 gms., 10 mmol) of ethyl trifluorothiolacetate. Remove the methanol by evaporation in vacuo, then add water until the reaction volume is 300 ml. Pass hydrogen sulfide through the reaction solution, then filter the resultant cupric sulfide precipitate through a Celite pad to obtain a solution containing 6′-N-trifluoroacetylsisomicin, which is used as is in the procedure of Example 13B.

B.
1,3,2',3''-Tetra-N-Acetyl-6'-N-Trifluoroacetylsisomicin

To the solution obtained in Example 13A add 300 ml. of methanol, then add acetic anhydride (109 ml., 1.16 Mol, 13.2 equivalents) adjusting the pH of the reaction mixture to 8.5 with triethylamine prior to adding the last 10 ml. of acetic anhydride. Stir for 18 hours at room temperature, then evaporate in vacuo to a residue comprising 1,3,2',3''-tetra-N-acetyl-6'-N-trifluoroacetylsisomicin.

C. 1,3,2',3''-Tetra-N-Acetylsisomicin

Dissolve the 1,3,2',3''-tetra-N-acetyl-6'-N-trifluoroacetylsisomicin prepared in Example 12B in 500 ml. of concentrated ammonium hydroxide. Stir at room temperature overnight and evaporate in vacuo. Dissolve the resultant residue in water and stir the solution with Amberlite IRA-401S (OH⊖) ion exchange resin. Remove the resin by filtration, wash with methanol, then evaporate the combined filtrate and methanol wash in vacuo followed by chromatography of the resultant residue on a 1.7 kilogram silica gel column (7.5×165 cm.) eluting with the lower phase of a chloroform:methanol:ammonium hydroxide (28%) (2:1:1) solvent system. Combine the like fractions containing the desired product as determined by thin layer chromatography and evaporate the combined eluates to a residue comprising 1,3,2',3''-tetra-N-acetylsisomicin, yield 29.9 gms., (55% theory); $[\alpha]_D^{26}+207.4°$ (c, 0.3 in water); pmr (ppm) (D$_2$O): $\delta$1.07, 1.17 (4''-C-$\underline{CH_3}$); 1.95, 1.98, 2.03 (N-acetyls); 3.13, 3.00 (3''-N-$\underline{CH_3}$); 5.29 (H-1'', $J_{1'',2''}=4.0$ Hz); 5.64 (H-1', $J_{1',2'}=2.5$ Hz); mass spectrum: (M+.) m/e 615, also m/e 598; 592; 550; 443, 425, 415, 397; 453, 411; 275, 257, 247, 229; 202; 169. Analysis calculated for: C$_{27}$H$_{45}$O$_{11}$N$_5$.1.5 H$_2$O: C, 50.43; H, 7.52; N, 10.89%. Found: C, 50.61; H, 7.36; N, 10.79%.

EXAMPLE 14

ISOLATION OF AMINOCYCLITOL-AMINOGLYCOSIDE TRANSITION METAL SALT COMPLEXES

A. Isolation of Gentamicin B-dicupric acetate Complex

Add cupric acetate hydrate (0.4 gms., 2 mmol) to a solution of gentamicin B (0.482 gms., 1 mmol) in methanol (25 ml.), stir for 30 minutes at room temperature then evaporate the solvent in vacuo and dry the resultant residue at 60° C. in vacuo to obtain gentamicin B-dicupric acetate complex as a deep blue colored solid (in contrast to green colored cupric acetate dihydrate); yield 0.8 gms.; $\lambda_{max}^{nujol}$ 6.42, 8.72, 13.90 m$\mu$.

B. Isolation of Gentamicin B-dicobalt (II) Acetate Complex (1) Dissolve gentamicin B (0.482 gms., 1 mmol) in dimethylsulfoxide (20 ml.) and add cobalt (II) acetate tetrahydrate (0.598 gms., 2 mmol). Stir for 30 minutes at room temperature and then pour into ether (30 ml.). Decant the ether layer and triturate the residue with fresh ether (20 ml.). Repeat this process once more, then triturate with ethyl ether. Isolate the resultant solid by filtration, wash with ethyl ether and dry to obtain gentamicin B-dicobalt (II) acetate complex as a lavender colored solid (in contrast to pink colored cobalt (II) acetate tetrahydrate), yield 0.8 gms. $\lambda_{max}^{nujol}$ 5.88, 6.36, 10.59, 12.42, 12.92, 13.90$\mu$.

(2) Dissolve the above isolated gentamicin B-dicobalt (II) acetate complex in dimethylsulfoxide and treat with N-(benzyloxycarbonyloxy)succinimide in a manner similar to that described in Example 11B followed by isolation and purification in the described manner to obtain 3,6'-di-N-benzyloxycarbonylgentamicin B. C. In a manner similar to that described in Examples 14A and 14B, treat gentamicin B with nickel (II) acetate tetrahydrate and with cadmium (II) acetate dihydrate and isolate and purify the complexes thereby formed to obtain gentamicin B-dinickel (II) acetate complex and gentamicin B-dicadmium (II) acetate complex.

In similar manner each of the aminocyclitolaminoglycoside transition metal salt complexes prepared in situ in the preceding Examples may be isolated.

EXAMPLE 15

REACTION OF 1,3-DI-DE-N-AMIDINODIHYDROSTREPTOMYCIN WITH N-BENZYLOXYCARBONYLOXYPHTHALIMIDE WITH AND WITHOUT CUPRIC ACETATE COMPLEX

A. 1,3-Di-De-N-Amidinodihydrostreptomycin

Add a solution of dihydrostreptomycin sulfate (25 gms., 0.0171 mmol) in water (100 ml.) to a solution of barium hydroxide (54 gms.) dissolved in water (600 ml.). Separate the barium sulfate thereby formed by filtration and heat the filtrate at reflux temperature under an atmosphere of nitrogen for 62 hours. To the cooled reaction mixture add 4 N sulfuric acid dropwise until the reaction mixture reaches a pH of 7. Separate the barium sulfate thereby formed by filtration, add Amberlite IRA-401S (OH⊖) resin to the filtrate and heat the mixture until the filtrate reaches a pH of 10. Remove the water by distillation and chromatograph the resultant residue on silica gel (600 gms.) eluting with a solvent mixture of chloroform/methanol/28% ammonium hydroxide (3:4:2). Collect the like fractions containing 1,3-di-de-N-amidinodihydrostreptomycin as determined by thin layer chromatography and evaporate the combined eluates to a residue of 1,3-di-de-N-amidinodihydrostreptomycin (yield-10.9 gms.).

B. Reaction of 1,3-Di-De-N-Amidinodihydrostreptomycin Via Cupric Acetate Complex with N-Benzyloxycarbonyloxyphthalimide to Produce 2''-N-Benzyloxycarbonyl-1,3-di-de-N-Amidinodihydrostreptomycin To a solution of 1,3-di-de-N-amidinodihydrostreptomycin (5 gms., 10 mmol) in dimethylsulfoxide (200 ml.) add cupric acetate monohydrate (2 gms., 10 mmol) and stir at room temperature for 15 minutes, then to the cupric salt complex thereby formed add dropwise with continuous stirring of the reaction mixture N-benzyloxycarbonyloxyphthalimide (5.5 gms.) in dimethylsulfoxide (20 ml.). Continue stirring for 2 hours, then pour the reaction mixture into diethyl ether (2 liters). Decant the supernatant ether and repeat the foregoing process using 1 liter and 500 ml. of diethyl ether, respectively. Dissolve the resultant gummy residue in a solvent mixture comprising methanol (150 ml.) and 28% ammonium hydroxide (10 ml.). Bubble hydrogen sulfide hrough the solution and separate the resultant precipitate of cupric sulfide by filtration through a pad of Celite, evaporate the filtrate and chromatograph the resultant residue on silica gel (400 gms.) eluting with a solvent mixture of chloroform/methanol/28% ammonium hydroxide (2:1:0.35). Combine the like eluates containing the desired compound as determined by thin layer chromatography and concentrate the combined eluates to a residue comprising 2″-N-benzyloxycarbonyl-1,3-di-de-N-amidinodihydrostreptomycin, yield 6 gms. (98% theory); $[\alpha]_D^{26}$ −96.5° (c, 0.5 in water). pmr (ppm) (D$_2$O): δ 1.21 (d, 4′-C-$\underline{CH_3}$, J=6 Hz); 3.04 (s, 2″-N-$\underline{CH_3}$); 5.13 (s, C$_6$H$_5\underline{CH_2}$OCONH); 7.41 (s, $\underline{C_6H_5}$CH$_2$OCONH); Analysis Calculated for: C$_{27}$H$_{43}$O$_{14}$N$_3$.H$_2$O; Calc.: C, 49.76; H, 6.96; N, 6.45. Found: C, 49.69; H, 6.78; N, 6.27. CD: $[\theta]_{TACu}^{285}$=+7,320.

C. Reaction of 1,3-Di-De-N-Amidinodihydrostreptomycin with N-Benzyloxycarbonyloxyphthalimide Without Cupric Acetate Complex Whereby is Produced 1-N-Benzyloxycarbonyl-1,3-Di-De-N-Amidinodihydrostreptomycin To a solution of 1,3-di-de-N-amidinodihydrostreptomycin (1 gm., 2.0 mmol) in N,N-dimethylformamide (40 ml.) add a solution of N-benzyloxycarbonyloxyphthalimide (0.8 gms., 2.7 mmol) in N,N-dimethylformamide (4 ml.). Stir the reaction mixture for 1 hour, then add water (10 ml.) and Amberlite IRA-401S (OH$^\ominus$) resin until the pH of the reaction mixture reaches 8.5. Separate the resin by filtration, remove the solvents by distillation, then chromatograph the resultant residue on silica gel (100 gms.) eluting with a solvent mixture of chloroform/methanol/28% ammonium hydroxide (2:1:0.35). Collect the like eluates containing 1-N-benzyloxycarbonyl-1,3-di-de-N-amidinodihydrostreptomycin as determined by thin layer chromatography and evaporate the combined eluates to a residue of 1-N-benzyloxycarbonyl-1,3-di-de-N-amidinodihydrostreptomycin, yield 0.417 gms. (33% theory); $[\alpha]_D^{26}$−93.6° (c, 0.55% in water). pmr (ppm) (D$_2$O): δ 1.22 (d, 4′-C-$\underline{CH_3}$, J=6 Hz); 2.42 (s, 2″-N-$\underline{CH_3}$); 5.12 (s, C$_6$H$_5\underline{CH_2}$OCONH); 7.40 (s, $\underline{C_6H_5}$CH$_2$OCONH); Analysis calculated for: C$_{27}$H$_{43}$O$_{14}$N$_3$.H$_2$O; Calcd.: C, 49.76; H, 6.96; N, 6.45. Found: C, 49.41; H, 6.55; N, 6.21. CD: $[\theta]_{TACu}^{282}$=+11,100.

PREPARATION OF 1-N-ALKYLAMINOGLYCOSIDES USING SELECTIVELY BLOCKED INTERMEDIATES

EXAMPLE 16

CONVERSION OF 3,2′,6′-TRI-N-ACETYLSISOMICIN TO 1-N-ETHYLSISOMICIN

A. 3,2′,6′-Tri-N-Acetyl-1-N-Ethylsisomicin

Add 0.1 N hydrochloric acid to a stirred solution of 3,2′,6′-tri-N-acetylsisomicin (1.146 gms., 2 mmol) in 20 ml. of water so as to bring the pH of the solution to 2.7. Cool the reaction mixture to 3° C. and add 2.2 ml. of a 1 molar solution of acetaldehyde in tetrahydrofuran (2.2 mmol), then add dropwise a solution of sodium cyanoborohydride (0.16 gms., 2.6 mmol) in 2 ml. of water. Stir the reaction mixture for one hour maintaining the temperature below 5° C. and the pH at about 2.7 by the addition of 0.1 N hydrochloric acid, then add 0.44 ml. of a 1 molar solution of acetaldehyde in tetrahydrofuran (0.44 mmol) followed by a solution of sodium cyanoborohydride (35 mg., 0.56 mmol) in a few drops of water, maintaining the pH at 2.7 by the addition of 0.1 N hydrochloric acid. Continue stirring the reaction mixture for one hour and repeat 2 times the foregoing addition of 0.22 ml. of acetaldehyde solution and 10 mg. of sodium cyanoborohydride. Continue stirring at room temperature for 18 hours, then bring the solution to a pH of 9 by stirring the solution with Amberlite IRA-401S ion exchange resin in the hydroxide form. Remove the resin by filtration, wash with water and concentrate the combined filtrate and washings in vacuo, and chromatograph the resultant residue on 100 gms. of silica gel (60-200 mesh) eluting with chloroform:methanol:ammonium hydroxide (30:10:0.2). Combine the like fractions as determined by thin layer chromatography on silica gel or using the same solvent system as above but in the proportion of 30:10:1 and concentrate in vacuo the combined eluates containing the major product and lyophilize the resultant aqueous mixture to a residue comprising 3,2′,6′-tri-N-acetyl-1-N-ethylsisomicin, yield 0.84 gms. (70% theory); $[\alpha]_D^{26}$+165° (c, 0.8 in water); pmr (ppm) (D$_2$O): δ 1.05 (CH$_2\underline{CH_3}$, J=17.0 Hz); 1.17 (4″-C-$\underline{CH_3}$); 1.84, 1.9, 1.91 (N-acetyls); 2.52 (3″-N-$\underline{CH_3}$); 4.80 (H-4′); 4.92 (H-1″, J$_1$″,2″=4.0 Hz); 5.4 (H-1′, J$_{1',2'}$=2.5 Hz); mass spectrum: (M$^+$.) m/e 601, (M+1)$^+$ m/e 602; also m/e 402; 392, 374, 160; 471, 453, 443, 425; 211; and 261. Analysis calculated for: C$_{27}$H$_{47}$N$_5$O$_{10}$.1.5H$_2$O: C, 51.58; H, 8.02; N, 11.14%. Found: C, 51.47; H, 8.89; N, 10.91%.

B. 1-N-Ethylsisomicin

Add 3,2′,6′-tri-N-acetyl-1-N-ethylsisomicin (0.1 gm.) to 10 ml. of 1 N sodium hydroxide and heat the solution under an atmosphere of nitrogen at reflux temperature until thin layer chromatographic analysis of an aliquot on silica gel using a 2:1:0.35 mixture of chloroform:methanol:ammonium hydroxide as the developing system indicates essential completion of de-N-acetylation (about 48 hours). Cool the reaction solution, add water until the volume is at about 50 ml., stir with Amberlite IRC-50 ion exchange resin in the proton form (which has been washed with water) until the pH is at about 5.5. Remove the resin by filtration, wash with water and stir the resin with 100 ml. of 7% aqueous ammonium hydroxide for about 30 minutes, decant the supernatant solution, and repeat the foregoing procedure twice using 50 ml. of 7% aqueous ammonium hydroxide each time then remove the resin by filtration. Combine the ammonium hydroxide filtrate and decantations, concentrate in vacuo and extract the resultant residue with methanol. Combine the methanol extracts and concentrate in vacuo, dissolve the resultant residue in a solvent mixture consisting of chloroform:methanol:ammonium hydroxide (2:1:0.35) and pass the solution through a column of alumina (8 gms., 0.8 cm.×30 cm. column), eluting with the same chloroform:methanol:ammonium hydroxide solvent mixture. Combine the like eluates as determined by thin layer chromatography and evaporate the combined eluates containing 1-N-ethylsisomicin and lyophilize the resultant aqueous mixture to a residue comprising 1-N-ethylsisomicin (71 mg.) (90% yield).

C. Conversion of Sisomicin to 1-N-Ethylsisomicin Without Purification of the Intermediates (1) 3,2′,6′-Tri-N-Acetylsisomicin Add cupric acetate hydrate (3 gms., 15 mmol) to a stirred solution of sisomicin (0.447 gms., 1 mmol) in water (5.33 ml.) and dimethylformamide (18 ml.). Stir at room temperature for 30 minutes, then add dropwise at the rate of about a drop every three seconds 3.1 ml. of a 1 molar solution of acetic anhydride in dimethylformamide (3.1 mmol). Stir an additional 30 minutes, then add 10 ml. of water and bubble hydrogen sulfide through the solution. Stir the reaction mixture for 30 minutes, then filter the precipitated cupric sulfide through a pad of Celite, wash the resultant cupric sulfide residue with water, and bring the combined filtrate to pH 9 by stirring with Amberlite IRA-401S ion exchange resin in the hydroxide cycle. Remove the resin by filtration, wash with water and concentrate the combined filtrate and washings to a residue comprising 3,2',6'-tri-N-acetylsisomicin.

(2) 3,2',6'-Tri-N-Acetyl-1-N-Ethylsisomicin

Dissolve the product of Example 16C(1) in 10 ml. of water and add 0.1 N hydrochloric acid until the solution is at a pH of about 2.7. Cool the reaction mixture to about 3° C. and add 0.73 ml. of 1 molar solution of acetaldehyde in tetrahydrofuran (0.73 mmol), then add dropwise a solution of 0.55 gms. of sodium cyanoborohydride in 0.7 ml. of water. Stir for one hour maintaining the pH of the solution at about 2.7 by the addition of 0.1 N hydrochloric acid, then add 0.15 ml. of a 1 molar solution of acetaldehyde in tetrahydrofuran (0.15 mmol) followed by a solution of 12 mg. of sodium cyanoborohydride in a few drops of water, again maintaining the pH at about 2.7. Repeat the foregoing procedure twice using each time 0.7 ml. of a 1 molar solution of acetaldehyde in tetrahydrofuran and 3 mg. of sodium cyanoborohydride. Stir at room temperature overnight, then bring the solution to a pH of about 9 with 1 N sodium hydroxide. Concentrate the solution in vacuo to a residue comprising 3,2',6'-tri-N-acetyl-1-N-ethylsisomicin.

(3) 1-N-Ethylsisomicin

Dissolve the 3,2',6'-tri-N-acetyl-1-N-ethylsisomicin obtained in Example 16C(2) in 60 ml. of 1 N sodium hydroxide and heat at reflux temperature under an atmosphere of nitrogen for 48 hours. Cool and bring the reaction mixture to a pH of about 5.5 by adding Amberlite IRC-50 ion exchange resin in the proton form. Remove the resin by filtration and wash with water. Stir the resin with 100 ml. of 7% aqueous ammonium hydroxide solution for 30 minutes, decant the solution and repeat the foregoing procedure twice using 100 ml. of 7% ammonium hydroxide each time, then filter. Combine the ammonium hydroxide filtrate with the decantations and evaporate in vacuo, and chromatograph the resultant residue on a column of silica gel (25 gms.) eluting with a solvent mixture of chloroform:methanol:ammonium hydroxide (2:1:0.34). Combine the like fractions as determined by thin layer chromatography on silica gel using the same solvent system and concentrate in vacuo the combined eluates containing 1-N-ethylsisomicin and lyophilize the resultant aqueous mixture to a residue of 1-N-ethylsisomicin, yield 0.233 gms. (49% theory).

EXAMPLE 17

CONVERSION OF 3,2',6'-TRI-N-ACETYLAMINOGLYCOSIDES TO 1-N-ETHYLAMINOGLYCOSIDES

A. 3,2',6'-Tri-N-Acetyl-1-N-Ethylverdamicin

Dissolve 3,2',6'-tri-N-acetylverdamicin (880 mg., 1.5 mmol) in water (15 ml.) and adjust the pH to 2.7 using 0.1 N hydrochloric acid (approximately 28 ml.). Cool in an ice bath to 8°–10° C., then while stirring add aqueous acetaldehyde (4.1 ml. of 0.73 molar acetaldehyde) in water (2 equivalents). Stir for 5 minutes at 8° C., then add dropwise a solution of sodium cyanoborohydride (182 mg., 3 mmol, 2 equivalents) in 2.5 ml. of water, adjusting the pH of the solution to 2.7 with 0.1 N hydrochloric acid. Continue maintaining the pH at about 2.7 by addition of 0.1 N hydrochloric acid until the reaction is complete as determined by thin layer chromatography. Allow the reaction mixture to stand at room temperature for 18 hours, then freeze dry the reaction mixture and chromatograph the resultant residue on silica gel (90 gm.) in a 1.5×126 cm. column eluting with chloroform:methanol:ammonium hydroxide (28%) (30:10:1). Combine the like fractions containing 3,2',6'-tri-N-acetyl-1-N-ethyl-verdamicin as determined by thin layer chromatography. Evaporate the combined eluates in vacuo to a residue of 3,2',6'-tri-N-acetyl-1-N-ethylverdamicin, yield 550 mg. (0.84 mmol, 56% theory); mass spectrum: m/e 485, 467, 457, 439; 420, 402, 392, 374; 261, 243, 233, 215, 183.

B. 1-N-Ethylverdamicin

Treat 3,2',6'-tri-N-acetyl-1-N-ethylverdamicin (200 mg., 0.304 mmol) with 1 N sodium hydroxide (20 ml.) at reflux temperature under an atmosphere of nitrogen, then isolate and purify the resulting product in a manner similar to that described in Example 16B to obtain 1-N-ethylverdamicin, yield 88 mg. (59% theory).

C. Conversion of 3,2',6'-Tri-N-Acetylaminoglycosides to the Corresponding 1-N-Ethyl Derivatives Thereof In the procedure of Example 16A instead of 3,2',6'-tri-N-acetylsisomicin utilize as starting compounds each of the 3,2',6'-tri-N-acetylaminoglycoside derivatives prepared in above Example 3A. Isolate and purify each of the resultant products in the manner described to obtain the corresponding 1-N-ethyl derivative of each of the 3,2',6'-tri-N-acetylaminoglycosides.

D. 1-N-Ethylaminoglycosides

In a manner similar to that described in Example 16B treat each of the 1-N-ethyl-3,2',6'-tri-N-acetylaminoglycoside derivatives prepared in above Example 4B with sodium hydroxide followed by isolation and purification of each of the resultant products in a manner similar to that described to obtain the corresponding unprotected 1-N-ethylaminoglycosides.

EXAMPLE 18

CONVERSION OF 3,6'-DI-N-SUBSTITUTED AMINOGLYCOSIDES TO THE CORRESPONDING 3,6'-DI-N-UNSUBSTITUTED-1-N-ALKYLAMINOGLYCOSIDES

A. Conversion of 3,6'-Di-N-Tert.-Butoxycarbonylgentamicin B to 1-N-Ethylgentamicin B To a stirred solution of 3,6'-di-N-tert.-butoxycarbonylgentamicin B (1.36 gms.) in water (15 ml.) add a 1 molar solution of acetaldehyde in tetrahydrofuran (2 ml.). Adjust the pH of the solution to about 4.9 with 0.1 N hydrochloric acid. Add sodium cyanoborohydride (0.2 gm.) and periodically adjust the pH to about 4.9. Stir for 5 hours at room temperature, then evaporate the solution to dryness, add trifluoroacetic acid (10 ml.) to the resultant residue and let stand for 5 minutes. Pour the reaction solution into ether, isolate the resultant precipitate by filtration and wash with ether. Chromatograph the precipitate on 100 gm. of silica gel using chloroform:methanol:ammonium hydroxide (3:4:2) as the solvent mixture. Combine the like fractions containing 1-N-ethylgentamicin B as determined by thin layer chromatography, evaporate in vacuo, dissolve the resultant residue in water and lyophilize; yield 40% theory; $[\alpha]_D^{26} + 126.2°$ (c, 1 in water); pmr (ppm) (D$_2$O): δ 5.55 (H-1',J$_1'$,$_2'$=3.0 Hz); 5.05 (H-1'', J$_1''$,$_2''$=4 Hz); 2.9 (3''-N-CH$_3$); 1.05-1.5 (2 C-CH$_3$); mass spectrum: [M+1]$^+$ 511; also m/e 380, 352, 334; 378, 350, 332; 219, 191, 173. Analysis Calculated for: C$_{21}$H$_{42}$O$_{10}$N$_4$.2CO$_2$3-H$_2$O; C, 42.33; H, 7.41; N, 8.58%. Found: C, 42.37; H, 7.43; N, 8.81%.

B. Conversion of 3,6'-Di-N-Acetylaminoglycosides to the Corresponding 1-N-Ethyl Derivatives Thereof (1) In the procedure of Example 16A, instead of 3,2',6'-tri-N-acetylsisomicin, utilize as starting compounds each of the 3,6'-di-N-acetylaminoglycoside derivatives prepared in above Example 5A. Isolate and purify each of the resultant products in the manner described to obtain, respectively,
(1) 3,6'-di-N-acetyl-1-N-ethylkanamycin A,
(2) 3,6'-di-N-acetyl-1-N-ethylgentamicin B,
(3) 3,6'-di-N-acetyl-1-N-ethylgentamicin B$_1$,
(4) 3,6'-di-N-acetyl-1-N-ethylgentamicin B$_2$,
(5) 3,6'-di-N-acetyl-1-N-ethylgentamicin A$_3$,
(6) 3,6'-di-N-acetyl-1-N-ethyl-6'-N-methylkanamycin A.

(2) In a manner similar to that described in Example 16B, treat each of the 3,6'-di-N-acetyl-1-N-ethylaminoglycoside derivatives prepared in above Example 18B with sodium hydroxide followed by isolation and purification of each of the resultant products in a manner similar to that described, to obtain the corresponding unprotected 1-N-ethylaminoglycosides.

EXAMPLE 19

CONVERSION OF 3,2'-DI-N-ACETYLAMINOGLYCOSIDES TO 1-N-ETHYLAMINOGLYCOSIDES

A. 3,2'-Di-N-Acetyl-1-N-Ethylaminoglycosides

Treat each of the 3,2'-di-N-acetylaminoglycosides prepared in Example 6A in a manner similar to that described in Example 16A and isolate and purify each of the resultant products in a manner similar to that described to obtain, respectively,
(1) 3,2'-di-N-acetyl-1-N-ethylkanamycin C,
(2) 3,2'-di-N-acetyl-1-N-ethyl-Antibiotic G-418,
(3) 3,2'-di-N-acetyl-1-N-ethylgentamicin A,
(4) 3,2'-di-N-acetyl-1-N-ethylenegentamicin A$_1$,
(5) 3,2'-di-N-acetyl-1-N-ethylgentamicin X$_1$,
(6) 3,2'-di-N-acetyl-1-N-ethylgentamicin X$_2$.

B. 1-N-Ethylaminoglycosides

Treat each of the 3,2'-di-N-acetyl-1-N-ethylaminoglycosides of Example 19A with sodium hydroxide in the manner described in Example 16B followed by isolation and purification of each of the resultant products in a manner similar to that described to obtain the corresponding unprotected 1-N-ethylaminoglycosides.

EXAMPLE 20

CONVERSION OF 3,6'-DI-N-ACETYLSISOMICIN TO 1,2'-DI-N-ETHYLSISOMICIN

A. 3,6'-Di-N-Acetyl-1,2'-Di-N-Ethylsisomicin

In a manner similar to that described in Example 16A treat 3,6'-di-N-acetylsisomicin with about 2 molar equivalents of acetaldehyde in tetrahydrofuran followed by the dropwise addition of about 2 molar equivalents of sodium cyanoborohydride. Isolate and purify the resultant product in a manner similar to that described in Example 16A to obtain 3,6'-di-N-acetyl-1,2'-di-N-ethylsisomicin.

B. 1,2'-Di-N-Ethylsisomicin

In a manner similar to that described in Example 16B treat 3,6'-di-N-acetyl-1,2'-di-N-ethylsisomicin with sodium hydroxide under an atmosphere of nitrogen. Isolate and purify the resultant product in a manner similar to that described to obtain 1,2'-di-N-ethylsisomicin.

PREPARATION OF 1-N-(AMINOHYDROXYALKANOYLAMINO-GLYCOSIDES USING SELECTIVELY BLOCKED INTERMEDIATES

EXAMPLE 21

CONVERSION OF 3,6'-DI-N-TERT.-BUTOXYCARBONYLGENTAMICIN B TO 1-N-(γ-AMINO-α-HYDROXYBUTYRYL)GENTAMICIN B

A. 1-N-(S-γ-amino-α-hydroxybutyryl)gentamicin B (1) To a solution of 68.2 mg. (0.1 mmol) of 3,6'-di-N-tert.-butoxycarbonylgentamicin B (purified product of Example 11F) in water (1 ml.), add methanol (1 ml.), then add dropwise with stirring a solution (0.25 ml.) of N-(S-γ-benzyloxycarbonylamino-α-hydroxybutyryloxy)succinimide (0.1 mmol) in dimethylformamide (0.4 molar solution). Stir for 1 hour, then add additional N-(S-γ-benzyloxycarbonylamino-α-hydroxybutyryloxy)succinimide (0.125 ml.). Continue stirring the reaction mixture at room temperature for 18 hours, then concentrate in vacuo and dissolve the resultant residue in methanol (4 ml.) and water (16 ml.). Add 5% palladium-on-carbon catalyst (0.05 gm.) and hydrogenate at 55 psi overnight. Remove the solids by filtration through a pad of Celite, wash the Celite pad with water and concentrate the combined filtrates and washings to a small volume and lyophilize. Dissolve the resultant residue in trifluoroacetic acid (0.5 ml.) and set aside for 3 minutes. Pour the solution into excess ether, collect the precipitate by filtration, wash with ether and dry to give 1-N-(S-γ-amino-α-hydroxybutyryl)gentamicin B as the trifluoroacetate salt. Obtain the free base by dissolving the foregoing salt in water and stirring the solution with Amberlite IRA-401S (OH$^\ominus$) ion exchange resin. Filter and lyophilize the filtrate to obtain 1-N-(S-γ-amino-α-hydroxybutyryl)gentamicin B, yield 49.7 mg. (83% theory).

(2) From Crude 3,6'-Di-N-Tert.-Butoxycarbonylgentamicin B

To the 50 ml. solution comprising 3,6'-di-N-tert.-butoxycarbonylgentamicin B prepared in Example 11F, add 50 ml. of methanol. To this solution add dropwise with stirring 10 ml. of a 1 molar solution of 1-N-(S-γ- benzyloxycarbonylamino-α-hydroxybutyryloxy)succinimide in dimethylformamide. Stir for 1 hour and monitor the reaction by thin layer chromatography using chloroform:methanol:ammonium hydroxide (2:1:0.35). Add an additional 5 ml. of the 1 molar solution of 1-N-(S-γ-benzyloxycarbonylamino-α-hydroxybutyryloxy)succinimide and stir the reaction mixture for 10 hours. Concentrate the solution in vacuo and chromatograph the resultant residue on 300 gm. of silica gel using chloroform:methanol:ammonium hydroxide (30:10:0.5) as the eluting solvent. Combine the like fractions containing the 1-N-(S-γ-benzyloxycarbonylamino-α-hydroxybutyryl)-3,6'-di-N-tert.-butoxycarbonylgentamicin B and evaporate to a residue. Dissolve the residue in water (50 ml.) and methanol (18 ml.) and hydrogenate in the presence of 5% palladium-on-carbon (600 mg.) at 55 psi for 10 hours. Remove the catalyst by filtration through a pad of Celite and wash the residue with water. Combine the filtrate and washings and evaporate in vacuo to remove the methanol. Wash the resulting aqueous layer 3 times with chloroform (25 ml.) and concentrate the aqueous solution in vacuo and dry the resultant residue over phosphorous pentoxide in vacuo. Dissolve the resultant residue in a minimum amount of trifluoroacetic acid and set the solution aside for 3 minutes. Add ether and isolate the resultant precipitate by filtration. Wash the precipitate with ether and dry. Dissolve the solid in 30 ml. of water and bring the solution to about pH 8.5 by stirring with Amberlite IRA-401S (OH⊖) ion exchange resin. Remove the solid by filtration, wash with water, combine the filtrate and washings and lyophilize to give 1-N-(S-γ-amino-α-hydroxybutyryl)gentamicin B.

Alternatively, add sulfuric acid to bring the foregoing aqueous solution to about pH 4.5 and lyophilize to obtain the sulfate salt of 1-N-(S-γ-amino-α-hydroxybutyryl)gentamicin B; pmr (ppm) ($D_2O$): δ 1.3 (4''-C-$CH_3$); 2.9 (3''-N-$CH_3$); 4.28 (H-2''', J=9 Hz and 4 Hz); 5.16 (H-1'', $J_{1'',2''}$=3.5 Hz); 6.12 (H-1', $J_{1',2'}$=3.0 Hz).

B. 1-N-(R-γ-Amino-α-hydroxybutyryl)gentamicin B (1) To a solution of 3,6'-di-N-tert.-butoxycarbonylgentamicin B (3.41 gms., 5 mmol) in methanol (25 ml.) and water (25 ml.) add with stirring a solution of N-(R-γ-N-benzyloxycarbonylamino-α-hydroxybutyryloxy)-succinimide (1.8 gms., 5 mmol) in dimethylformamide (10 ml.). Stir the reaction mixture for 6 hours, concentrate in vacuo and chromatograph the resultant residue on silica gel (60–200 mesh, 300 gms.) using a solvent system comprising chloroform:methanol:ammonium hydroxide (30:10:0.25). Combine the like fractions containing the desired product as determined by thin layer chromatography, concentrate in vacuo and rechromatograph the residue on the same column using the same solvent system. Combine the like rechromatographed fractions and evaporate in vacuo to a residue comprising 1-N-(R-γ-N-benzyloxycarbonylamino-α-hydroxybutyryloxy)-3,6'-di-N-tert.-butoxycarbonylgentamicin B.

(2) Dissolve the product of Example 21B(1) in 50% aqueous methanol (20 ml.) and hydrogenate over 5% palladium-on-carbon catalyst (0.2 gms.) at room temperature and 50 psi for 24 hours. Remove the catalyst by filtration through a pad of Celite, wash the water and evaporate the combined filtrates in vacuo. Dissolve the resultant residue in trifluoroacetic acid (25 ml.) and set aside for 3 minutes. Add ether and isolate the resultant precipitate comprising the trifluoroacetic acid addition salt of 1-N-(R-γ-amino-α-hydroxybutyryl)gentamicin B, wash with ether and dry. Dissolve the dry precipitate in water (10 ml.) and stir with Amberlite IRA-401S (OH⊖) ion exchange resin, sufficient to place the pH to 9.5. Remove the resin by filtration, wash with water and lyophilize the combined filtrates to a residue comprising pure 1-N-(R-γ-amino-α-hydroxybutyryl)gentamicin B, yield 0.6 gms.; $[\alpha]_D^{26}$+118.1° (c, 1 in water). pmr (ppm) ($D_2O$): δ 1.23 (4''-C-$CH_3$); 2.66 (3''-N-$CH_3$); 4.2 (H-2''', J=5 Hz and 3 Hz); 5.03 (H-1'', J=4 Hz); 5.4 (H-1', J=3.5 Hz). Analysis calculated for: $C_{23}H_{45}O_{12}N_5 \cdot 3CO_2 \cdot 4H_2O$; C, 39.64; H, 6.78; N, 8.89%. Found: C, 39.88; H, 6.58; N, 9.28%.

EXAMPLE 22

CONVERSION OF 3,6'-DI-N-TERT.-BUTOXYCARBONYLGENTAMICIN B TO 1-N-(S-β-AMINO-α-HYDROXYPROPIONYL)-GENTAMICIN B

A.

1-N-(S-β-N-Benzyloxycarbonylamino-α-Hydroxypropionyl)-3,6'-Di-N-Tert.-Butoxycarbonylgentamicin B Add to a stirring solution of 3,6'-di-N-tert.-butoxycarbonylgentamicin B (11.28 g., 16.4 mmol) in methanol (100 ml.) and water (100 ml.), a solution of N-(S-β-benzyloxycarbonylamino-α-hydroxypropionyloxy)succinimide (10 g., 30 mmol) in 40 ml. of N,N-dimethylformamide over a fifteen minute period. After a period of two hours, evaporate off the solvents in vacuo at 50° C. Chromatograph the resultant residue on 500 g. of silica gel using a 30:10:0.5 ratio of chloroform:methanol:concentrated ammonium hydroxide to obtain 13.22 g. of 1-N-(S-β-benzyloxycarbonylamino-α-hydroxypropionyl)-3,6'-di-N-tert.-butoxycarbonylgentamicin B.

B. 1-N-(S-β-amino-α-hydroxypropionyl)gentamicin B

Hydrogenate the product of Example 22 at 50 psi at room temperature in a mixture of water (730 ml.) and methanol (240 ml.) in the presence of 0.7 g, 5% palladium-on-carbon catalyst for 24 hours. Remove the catalyst by filtration through a pad of Celite and wash with water. Concentrate the combined filtrates and dry the residue thoroughly. Dissolve the product in trifluoroacetic acid (80 ml.) and set aside for 3 minutes. Pour the solution into excess ether (2 l.) to precipitate the trifluoroacetic acid salt of pure 1-N-(S-β-amino-α-hydroxypropionyl)gentamicin N. Isolate by filtration, wash with ether and dry. Treat the product with Amberlite IRA-401S (OH⊖) resin in water to pH 9, filter the solution, wash the resin and lyophilize the combined solution to give 1-N-(S-β-amino-α-hydroxypropionyl)gentamicin B; $[\alpha]_D^{26}$+112.5° (c, 0.4 in water); pmr (ppm) ($D_2O$): δ 1.15 (4''-C-$CH_3$); 1.36 (H-2ax, $J_{1,2}=J_{2,3}=J_{1ax,1eq}$=12.5 Hz); 1.90 (H-2eq); 2.45 (3''-N-$CH_3$); 4.06 (H-5''eq, $J_{5''eq,ax}$=13.0 Hz); 4.13 (H-2''', $J_{2''',3'''}$=~4.0 and 7.0 Hz); 5.05 (H-1'', $J_{1'',2''}$=4.0 Hz); 5.32 (H-1', $J_{1',2'}$=3.0 Hz). Yield=near quantitative.

C. Carry out the procedures of Examples 22A and 22B utilizing N-(S-δ-benzyloxycarbonylamino-α-hydroxyvaleryloxy)succinimide instead of the succinimide reagent specified in Example 22A, whereby is obtained 1-N-(S-δ-amino-α-hydroxyvaleryl)gentamicin B.

EXAMPLE 23

CONVERSION OF 3,6'-DI-N-BENZYLOXYCARBONYLAMINO-GLYCOSIDES TO 1-N-(S-γ-AMINO-α-HYDROXYBUTYRYL)AMINOGLYCOSIDES

A. Preparation of 1-N-(S-γ-Amino-α-Hydroxybutyryl)kanamycin A (1) To a stirred solution of 3,6'-di-N-benzyloxycarbonylkanamycin A (1.54 gms., 2 mmol) in tetrahydrofuran (20 ml.) and water (20 ml.) add dropwise a solution of N-(S-γ-benzyloxycarbonylamino-α-hydroxybutyryloxy)succinimide (1.163 gms., 3 mmol) in 2 ml. of N,N-dimethylformamide. Stir for two hours, then concentrate in vacuo and chromatograph the resultant syrupy residue on silica gel (150 gms.) eluting with chloroform:methanol:concentrated ammonium hydroxide (2:1:0.35) solvent mixture. Combine the like fractions containing the desired product as determined by thin layer chromatography and evaporate the combined eluates in vacuo to a residue comprising 1-N-(S-γ-benzyloxycarbonylamino-α-hydroxybutyryl)-3,6'-di-N-benzyloxycarbonylkanamycin A; yield 1.3 gm.

(2) Hydrogenate the product of Example 23A(1) in aqueous methanol (1:1) (20 ml.) in the presence of 5% palladium-on-charcoal (0.10 gms.) for 3 hours. Separate the catalyst by filtration and evaporate the resultant filtrate in vacuo to a residue comprising 1-N-(S-γ-amino-α-hydroxybutyryl)kanamycin A in quantitative yields.

B. In the procedure of Example 23A, substitute N-(S-β-benzyloxycarbonylamino-α-hydroxypropionyloxy)succinimide for N-(S-γ-benzyloxycarbonylamino-α-hydroxybutyryloxy)succinimide to obtain 1-N-(S-β-amino-α-hydroxypropionyl)kanamycin A in an overall yield of greater than 50% theory.

C. Treat each of the 3,6'-di-N-benzyloxycarbonylaminoglycoside products of Example 11E in a manner similar to that described in above Example 23A to obtain, respectively, (1) 1-N-(S-γ-amino-α-hydroxybutyryl)gentamicin $B_1$,
(2) 1-N-(S-γ-amino-α-hydroxybutyryl)gentamicin $A_3$,
(3) 1-N-(S-γ-amino-α-hydroxybutyryl)-6'-N-methylkanamycin A.

EXAMPLE 24

CONVERSION OF 3,6'-DI-N-BENZYLOXYCABONYLGENTAMICIN B TO 1-N-(S-β-AMINO-α-HYDROXYPROPIONYL)-GENTAMICIN B AND TO 1-N-(R-β-AMINO-α-HYDROXYPROPIONYL)-GENTAMICIN B

A. 1-N-(S-β-Amino-α-Hydroxypropionyl)gentamicin B

To a solution of 3,6'-di-N-benzyloxycarbonylgentamicin B (3.75 gms., 5 mmol) in methanol (25 ml.) and water (25 ml.), add with stirring a solution of N-(S-β-benzyloxycarbonylamino-α-hydroxypropionyloxy)succinimide (2.18 gms., 6.5 mmol) in dimethylformamide (12 ml.). Stir the reaction mixture for 2 hours, concentrate in vacuo, and dissolve the resultant residue in water (75 ml.) and methanol (75 ml.). Hydrogenate in the presence of 5% palladium on charcoal (5 gms.) at 50 psi for 24 hours. Remove the catalyst by filtration through a pad of Celite and wash with water. Concentrate the combined filtrate and washings and chromatograph the resultant residue on Dowex-1×2 ion exchange resin (200 gm., 200–400 mesh) in the hydroxide form eluting with water. Combine the like fractions containing 1-N-(S-β-amino-α-hydroxypropionyl)gentamicin B as determined by thin layer chromatography on silica gel using chloroform:methanol:ammonium hydroxide (3:4:2) as the solvent system. Concentrate to a small volume, dilute with water and lyophilize to obtain 1-N-(S-β-amino-α-hydroxypropionyl)gentamicin B, yield 1.7 gms. (60% theory).

B. 1-N-(R-β-Amino-α-Hydroxypropionyl)gentamicin B

In a manner similar to that described in Example 24A treat 3,6'-di-N-benzyloxycarbonylgentamicin B with 1-N-(R-β-benzyloxycarbonylamino-α-hydroxypropionyloxy)succinimide and isolate and purify the resultant product in a manner similar to that described to obtain 1-N-(R-β-amino-α-hydroxypropionyl)-gentamicin B.

C. Conversion of 3,6'-Di-N-Benzyloxycarbonylgentamicin B to 1-N-(S-β-Amino-α-Hydroxypropionyl)gentamicin B and 1-N-(R-β-Amino-α-Hydroxypropionyl)gentamicin B Using Racemic β-N-Benzyloxycarbonylamino-α-Hydroxypropionic Acid (1) To a stirred solution of 3,6'-di-N-benzyloxycarbonylgentamicin B (1 gm., 1.33 mmol) in methanol (5 ml.) and water (5 ml.) add a solution of racemic N-(β-benzyloxycarbonylamino-α-hydroxypropionyloxy)succinimide (0.674 gms., 0.2 mmol) in dimethylformamide (2 ml.). Stir for 2 hours, then evaporate the solvent in vacuo. Chromatograph the resultant residue on silica gel (60–100 mesh, 100 gms.) eluting with a mixture of chloroform:methanol:ammonium hydroxide (30:10:1). Monitor the fractions by thin layer chromatography on silica gel using chloroform:methanol:ammonium hydroxide (2:1:0.35) as solvent system. Combine the like fractions containing 1-N-(S-β-benzyloxycarbonylamino-α-hydroxypropionyl)-3,6'-di-N-benzyloxycarbonylgentamicin B, evaporate in vacuo, add water to the resultant residue and lyophilize from water, yield 0.42 gms. (65% theory). Similarly, combine the like fractions containing 1-N-(R-β-benzyloxycarbonylamino-α-hydroxypropionyl)gentamicin B, evaporate the solvents in vacuo, add water and lyophilize, yield 0.36 gms. (55.8% theory).

(2) Hydrogenate each of the two fractions separately in methanol (5 ml.) and water (5 ml.) in the presence of 5% palladium on charcoal catalyst at 55 psi for 24 hours. In each instance remove the catalyst by filtration through Celite, wash with water and evaporate the combined filtrates to the residue. Add water to the residue and lyophilize to obtain pure 1-N-(S-β-amino-β-hydroxypropionyl)gentamicin B and 1-N-(R-β-amino-α-hydroxypropionyl)gentamicin B, respectively, in near quantitative yields.

EXAMPLE 25

CONVERSION OF 3,6'-DI-N-BENZYLOXYCARBONYLGENTAMICIN B TO 1-N-(S-γ-AMINO-α-HYDROXYBUTYRYL)GENTAMICIN B AND 1-N-(R-γ-AMINO-α-HYDROXYBUTYRYL)GENTAMICIN B USING RACEMIC N-γ-BENZYLOXYCARBONYL-α-HYDROXYBUTYRIC ACID

In a manner similar to that described in Example 24C treat 3,6'-di-N-benzyloxycarbonylgentamicin B in aqueous methanol with a solution of racemic N-γ-benzyloxycarbonylamino-α-hydroxybutyryloxy)succinimide in dimethylformamide, then evaporate the reaction mixture in vacuo to a residue comprising 1-N-(R,S-γ-benzyloxycarbonylamino-α-hydroxybutyryl)-3,6'-di-N-benzyloxycarbonylgentamicin B. Chromatograph on silica gel in a manner similar to that described in Example 24C and combine the like fractions as determined by thin layer chromatography and evaporate each of the combined fractions in vacuo to a residue comprising 1-N-(S-γ-benzyloxycarbonylamino-α-hydroxybutyryl)-3,6'-di-N-benzyloxycarbonylgentamicin B and 1-N-(R-γ-benzyloxycarbonylamino-α-hydroxybutyryl)-3,6'-di-N-benzyloxycarbonylgentamicin B, respectively. Hydrogenate each of the two fractions in the presence of 5% palladium-on-charcoal catalyst similar to that described in Example 24C(2) to obtain 1-N-(S-γ-amino-α-hydroxybutyryl)gentamicin B and 1-N-(R-γ-amino-α-hydroxybutyryl)gentamicin B, respectively.

EXAMPLE 26

PREPARATION OF 3,6'-DI-N-(p-METHOXYBENZYLOXYCARBONYL)AMINOGLYCOSIDES AND CONVERSION TO 1-N-SUBSTITUTED DERIVATIVES

A. 3,6'-Di-N-p-Methoxybenzyloxycarbonyl-Gentamicin B

To a stirred solution of cobalt (II) acetate tetrahydrate (106.2 gms., 0.427 moles) in 2.5% aqueous dimethylsulfoxide (3 liters) add triethylamine (30 ml., 0.215 moles), followed by gentamicin B (72.3 gms., 0.15 moles). Stir the reaction mixture at room temperature for 30 minutes, then add dropwise over a period of an hour a solution of p-methoxybenzyl-S-(4,6-dimethylpyrimidin-2-yl)-thiol carbonate (91.2 gms., 0.3 moles) in dimethylsulfoxide (200 ml.). When the reaction is completed (usually about 4 hours) as determined by thin layer chromatography using as solvent system a mixture of chloroform/methanol/concentrated ammonium hydroxide (27:11:2.6 v/v/v), pour the mixture into ether (8 liters), mix thoroughly and set aside. Decant the clear, supernatant solution and repeat the foregoing procedure four times using 4 liters of ether each time. Dissolve the resultant gummy residue in methanol (500 ml.) and bubble hydrogen sulfide through the solution with stirring for about 30 minutes. Continue stirring the mixture for about 1 hour. Filter the reaction mixture through a pad of Celite over milipore filter, wash the Celite pad thoroughly with methanol (3×500 ml.) and stir the resultant filtrate with methanol-washed Amberlite IRA-401S (⊖OH) resin for 1 hour. Filter the mixture, wash the separated residue thoroughly with methanol (4 liters) and evaporate the combined filtrate and washings. Dissolve the resultant residue in methanol (200 ml.) and add the methanol solution dropwise to a stirred solution of a 1:1 mixture of ethyl acetate-ether (6 liters). Allow the solution to stand 18 hours at 4° C., then separate the resultant precipitate by filtration, wash the precipitate with ether and dry to obtain 3,6'-di-N-p-methoxybenzyloxycarbonyl-gentamicin B, yield 110 gms. (91% theory of purity greater than 95%). For analysis, further purify a small sample by chromatography on a column of silica gel (15 gms.) eluting with chloroform/methanol/concentrated ammonium hydroxide (27:11:2.6 v/v/v) (usually about 4 hours). Evaporate the combined eluates to a residue comprising analytically pure 3,6'-di-N-p-methoxybenzyloxycarbonyl-gentamicin B; $[\alpha]_D^{26} +109.2°$ (c, 1 in dimethylformamide). PMR (dmso-$d_6$) δ 1.22 (3H, s, C-Me), 2.52 (3H, s, N-Me), 6.87 (8H, dd centered at 6.87, aromatic hydrogens). $\nu_{max}^{methanol}$ (Nujol) 1700 (c=0), 3325 (OH, NH). Analysis calculated for: $C_{37}H_{54}N_4O_{16}.H_2O$: C, 53.61; H, 6.81; N, 6.75%. Found: C, 53.78; H, 6.88; N, 6.54%.

B. 3,6'-Di-N-p-Methoxybenzyloxycarbonyl-Kanamycin A

Dissolve kanamycin A (19.4 gms., 40 mmoles) and nickel (II) acetate (49.6 gms., 200 mmoles) in dimethylsulfoxide (800 ml.) and stir for 30 minutes. Add dropwise a solution of p-methoxybenzyl-S-(4,6-dimethylpyrimidin-2-yl)-thiolcarbonate (32 gms., 100 mmoles) in dimethylsulfoxide (70 ml.). Stir the reaction mixture for 6 hours, then pour into ether (2 liters) with stirring. Allow the resultant oil to settle and decant the supernatant liquid. Repeat this procedure two more times with 1 liter and 500 ml. of ether, respectively. Dissolve the resultant oily residue in methanol (800 ml.) and bubble hydrogen sulfide through the solution with stirring for about 30 minutes. Continue stirring the mixture for 1 hour, then filter the reaction mixture through a pad of Celite and evaporate the filtrate. Add ether to the resultant residue and stir the mixture until a solid gum is obtained. Allow the gum to settle, decant the supernatant liquid, and dissolve the gum in methanol. Add the methanol solution dropwise to 1 liter of ether with stirring. Separate the resultant precipitate by filtration, and dry to obtain essentially pure 3,6'-di-N-p-methoxybenzyloxycarbonyl-kanamycin A, yield 32.8 gms. (87.5% theory). For analysis, further purify a small sample by chromatography on silica gel eluting with the lower phase of a 1:1:1 (v/v/v) mixture of chloroform/methanol/concentrated ammonium hydroxide. Evaporate the combined eluates to a residue comprising analytically pure 3,6'-di-N-p-methoxybenzyloxycarbonyl-kanamycin A; calculated for: $C_{36}H_{52}O_{17}N_4.CO_2.2H_2O$; C, 49.77%; H, 6.32%; N, 6.28%. Found: C, 49.77%; H, 6.06%; N, 6.12%; $[\alpha]_D^{26} +66.4°$ (CH$_3$OH, 0.3%). pmr in dmso-$d_6$; δ3.74 (6H, s-OCH$_3$), 4.80 (4H, s-CH$_2$C$_6$H$_4$OCH$_3$), 6.87 (4H, m, C$_6$H$_4$OCH$_3$), 7.25 (4H, m, -C$_6$H$_4$OCH$_3$).

C. Conversion of 1-N-substituted Derivatives

Treat each of the compounds prepared in above Examples 26A and 26B in a manner similar to that described in each of Examples 18, and 21-25 to obtain the corresponding 1-N-substituted derivative described therein.

We claim:

1. A polyamino-organic compound-transition metal salt complex of a polyamino-organic compound devoid of substituents, other than amino or hydroxyl, readily reactable with transition metal salts or acylating agents, wherein at least one of said amino groups has an available neighboring hydroxyl group, and at least one other of said amino groups is devoid of an available neighboring hydroxyl group, or is less reactive to a neighboring hydroxyl group because of steric hindrance, said salt being a salt of a divalent transition metal cation selected from the group consisting of copper (II), nickel (II), cobalt (II), and cadmium (II), or a mixture of said salts, wherein said divalent transition metal salt is combined with said polyamino-organic compound as a complex between said divalent transition metal salt and said available neighboring amino and hydroxyl pairs, the number of complex sites being no greater than the number of said available neighboring amino and hydroxyl group pairs.

2. A complex of claim 1 which is an aminocyclitolaminoglycoside-transition metal salt complex wherein at least one of said amino groups has an available neighboring hydroxyl group and said salt is a salt of a divalent transition metal cation selected from the group consisting of copper (II), nickel (II), cobalt (II) and cadmium (II), or is a mixture of said salts, said aminocyclitol-aminoglycoside-transition metal salt complex having complex sites between said divalent transition metal salt and said available neighboring amino and hydroxyl group pairs, the relative molar quantity of said transition metal salt per mole of said aminocyclitol-aminoglycoside being no greater than the number of said available neighboring amino and hydroxyl group pairs.

3. A complex of claim 2 wherein said aminocyclitolaminoglycoside is a 4,6-di-O-(aminoglycosyl)-1,3-diaminocyclitol and said divalent transition metal cation is a member selected from the group consisting of copper (II), nickel (II) and cobalt (II).

4. A complex of claim 2 which is a 4,6-di-O-(aminoglycosyl)-1,3-diaminocyclitol containing one or two moles of said transition metal salt per mole of 4,6-di-O-(aminoglycosyl)-1,3-diaminocyclitol, said transition metal salt being an acetate salt of a transition metal cation selected from the group consisting of copper (II), nickel (II) and cobalt (II), said 4,6-di-O-(aminoglycosyl)-1,3-diaminocyclitol being a member selected from the group consisting of sisomicin, verdamicin, tobramycin, gentamicin A, gentamicin $A_1$, gentamicin $A_3$, gentamicin B, gentamicin $B_1$, gentamicin $C_1$, gentamicin $C_{1a}$, gentamicin $C_2$, gentamicin $C_{2a}$, gentamicin $C_{2b}$, gentamicin $X_2$, Antibiotic 66-40B, Antibiotic 66-40D, Antibiotic JI-20A, Antibiotic JI-20B, Antibiotic G-52, Antibiotic G-418; the 5-epi-, 5-deoxy-, and 5-epi-azido-5-deoxy analogs of the foregoing;

kanamycin A, kanamycin B, kanamycin C, 3',4'-dideoxykanamycin B, nebramycin factor 4, nebramycin factor 5', 6'-N-methylkanamycin A, 3',4'-dideoxy-6'-N-methylkanamycin B, and 3',4'-dideoxy-3',4'-dehydrokanamycin B.

5. A complex of claim 4 which is a sisomicin-transition metal salt complex having two moles of a transition metal salt selected from the group consisting of copper (II) acetate, cobalt (II) acetate and nickel (II) acetate per mole of sisomicin.

6. A complex of claim 4 which is a gentamicin B-transition metal salt complex having two moles of a transition metal salt selected from the group consisting of copper (II) acetate, cobalt (II) acetate and nickel (II) acetate per mole of gentamicin B.

7. A complex of claim 4 which is a kanamycin A-transition metal salt complex having two moles of a transition metal salt selected from the group consisting of copper (II) acetate, cobalt (II) acetate and nickel (II) acetate per mole of kanamycin A.

8. A composition comprising a polyamino-organic compound-transition metal salt complex of claim 1 and an inert, organic solvent.

9. A composition of claim 8 comprising an aminocyclitolaminoglycoside transition metal salt complex of claim 3 and an inert, organic solvent.

10. The process for preparing a composition of claim 8 which comprises the reaction of a polyamino-organic compound devoid of substituents, other than amino or hydroxyl, readily reactable with transition metal salts or acylating agents, wherein at least one of said amino groups has an available neighboring hydroxyl group, and at least one other of said amino groups is devoid of an available neighboring hydroxyl group, or is less reactive to a neighboring hydroxyl group because of steric hindrance, in an inert, organic solvent, with a salt of a divalent transition metal cation selected from the group consisting of copper (II), nickel (II), cobalt (II), and cadmium (II) or mixtures thereof in a molar quantity of said transition metal salt at least equal to the molar quantity of said polyamino-organic compound times the number of available, neighboring amino and hydroxyl group pairs therein, whereby a complex is formed between said transition metal salt and said available neighboring amino and hydroxyl group pairs of said polyamino-organic compound.

11. The process of claim 10 together with the subsequent step of isolating the thereby formed polyamino-organic compound-transition metal salt complex.

12. The process of claim 10 wherein said inert organic solvent contains water.

* * * * *